US008540139B2

(12) United States Patent
Dacey et al.

(10) Patent No.: US 8,540,139 B2
(45) Date of Patent: Sep. 24, 2013

(54) OUTER BOXES FOR STORING AND DELIVERING MEDICAL DEVICES USED DURING SURGICAL PROCEDURES AND METHODS THEREFOR

(75) Inventors: Denise Marie Dacey, Glen Gardner, NJ (US); Jonathan William Gillespie, Chatham, NJ (US)

(73) Assignee: Ethicon, Inc., Somerville, NJ (US)

( * ) Notice: Subject to any disclaimer, the term of this patent is extended or adjusted under 35 U.S.C. 154(b) by 268 days.

(21) Appl. No.: 12/820,469

(22) Filed: Jun. 22, 2010

(65) Prior Publication Data
US 2011/0309073 A1    Dec. 22, 2011

(51) Int. Cl.
*B65D 6/18*    (2006.01)

(52) U.S. Cl.
USPC .......................................... 229/103.3; 220/6

(58) Field of Classification Search
USPC ............ 229/103.3, 126, 77, 79, 82; 206/339, 206/483
See application file for complete search history.

(56) References Cited

U.S. PATENT DOCUMENTS

| 149,484 | A | | 4/1874 | Kelly et al. |
| 232,273 | A | | 9/1880 | Jaeger |
| 1,731,996 | A | * | 10/1929 | Appelbaum ................ 206/288 |
| 2,508,579 | A | * | 5/1950 | McFall ........................ 206/284 |
| 3,187,985 | A | | 6/1965 | Simjian |
| 3,257,127 | A | * | 6/1966 | Tilton, Jr. ...................... 281/31 |
| 3,301,463 | A | | 1/1967 | Locke |
| 3,482,765 | A | | 12/1969 | Probst, Sr. |
| 3,635,392 | A | | 1/1972 | Burgher |
| D257,829 | S | | 1/1981 | Webinger |
| 5,050,735 | A | | 9/1991 | Levy |
| 5,219,077 | A | | 6/1993 | Transeu |
| 5,249,682 | A | | 10/1993 | Transeu |
| 5,597,112 | A | | 1/1997 | Knapp |
| RE36,132 | E | | 3/1999 | Heacox |
| 6,003,758 | A | | 12/1999 | Mattia et al. |
| 6,045,035 | A | | 4/2000 | Murakami et al. |

(Continued)

FOREIGN PATENT DOCUMENTS

| DE | 20201750 | 8/2002 |
| GB | 04986 | 0/1910 |
| GB | 2254593 | 10/1992 |
| JP | 08143034 A | * 6/1996 |

OTHER PUBLICATIONS

International Search Report received in International Application No. PCT/US2011/041215, mailed Sep. 30, 2011.

*Primary Examiner* — Gary Elkins
*Assistant Examiner* — Christopher Demeree
(74) *Attorney, Agent, or Firm* — E. Richard Skula

(57) ABSTRACT

A box for a medical device includes a first panel, a second panel hingedly connected with a lower edge of the first panel, a third panel hingedly connected with a lower edge of the second panel, a first side flap hingedly connected with a first side of the first panel, and a second side flap hingedly connected with a second side of the first panel. The third panel is folded over the second panel and the second panel is folded over the first panel for forming a first storage compartment and a separate second storage compartment. The first and second side flaps are folded over the second panel for closing the sides of the box. The box includes a cover foldable over and interlockable with the first side flap, the second panel, and the second side flap for holding the cover closed and closing the box.

19 Claims, 23 Drawing Sheets

(56) References Cited

U.S. PATENT DOCUMENTS

| | | | |
|---|---|---|---|
| 6,505,737 B1 * | 1/2003 | Sherman | 206/308.1 |
| 6,578,757 B1 | 6/2003 | Espenshied et al. | |
| D479,464 S | 9/2003 | Kopecky | |
| 7,481,314 B2 | 1/2009 | Komarnycky | |
| 7,600,634 B2 | 10/2009 | Malinowski et al. | |

* cited by examiner

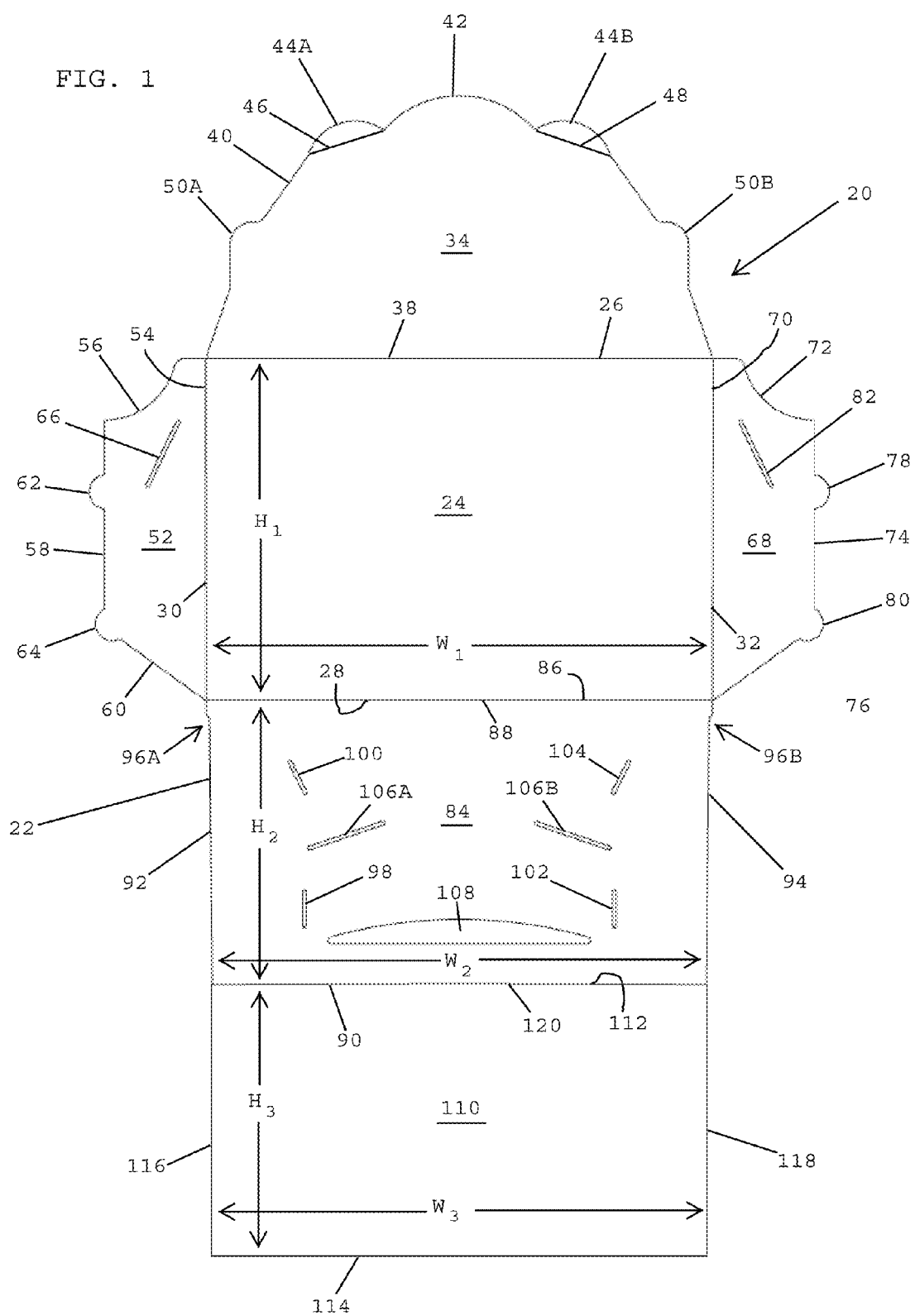

OUTER BOXES FOR STORING AND DELIVERING MEDICAL DEVICES USED DURING SURGICAL PROCEDURES AND METHODS THEREFOR

CROSS-REFERENCE TO RELATED APPLICATIONS

The present application is related to commonly assigned U.S. Design patent application Ser. No. 29/364,297, filed Jun. 22, 2010, the disclosure of which is hereby incorporated by reference herein.

BACKGROUND OF THE INVENTION

1. Field of the Invention

The present invention generally relates to medical devices, and more specifically relates to packages for storing medical devices.

2. Description of the Related Art

Surgical mesh is often used during surgical procedures for supporting tissue, such as supporting tissue during a hernia repair procedure. It has been observed that using surgical mesh to repair a hernia will promote more rapid healing and minimize the likelihood of hernia re-occurrence.

A surgical mesh is typically made from a biocompatible material such as polypropylene. The mesh may be covered with one or more absorbable layers for reducing the formation of adhesions. In many instances, surgical mesh products require proper packaging that enables the mesh to remain flat so that, when deployed, the mesh does not have any creases or folds. It is also critical that the packaging maintains the surgical mesh in a sterile condition, and that the packaging enables the mesh to be easily removed from the package and presented to surgical personnel in a simple and efficient manner.

Conventional surgical mesh packages typically position the mesh within some type of sealed container or pouch with the mesh being situated between a bottom package element and a top package element that are sealed together. To open the package, surgical personnel must physically separate the top element from the bottom element, usually requiring the separation of two, three, or even four edges. Thus, the steps involved to access the surgical mesh at the time it is needed are cumbersome and time consuming.

Some attempts have been made to reduce the size of surgical mesh packages by folding the mesh prior to placing it in a package. Folding the mesh, however, tends to form creases in the mesh, which may result in the mesh irritating the surrounding tissue.

Commonly assigned U.S. Pat. No. 5,249,682 to Transue, the disclosure of which is hereby incorporated by reference herein, teaches a package for holding a medical device such as a surgical mesh. In one embodiment, the medical device includes a surgical mesh having a mesh plug attached perpendicularly thereto. The mesh is substantially flat and lies in a plane which is substantially horizontal with respect to the plug. The package includes a folder that has a central floor panel for receiving the mesh and the mesh plug assembly. A first end panel is foldably connected to one side of the central panel for retaining the mesh on the central panel. At least one reinforcing panel is foldably connected to the first end panel for providing structural strength to the package. A connecting panel foldably connected to the opposite side of the central panel is, in turn, foldably connected to an optional plug retaining panel. The optional plug retaining panel is, in turn, foldably connected to a second end panel. The reinforcing panel is folded outwardly and locked to the first end panel with locking slots and tabs, the first end panel is locked to the central floor panel with locking slots and tabs, and the second end panel is locked to the central panel with locking slots and tabs.

Commonly assigned U.S. Pat. No. 7,481,314 to Komarnycky, the disclosure of which is hereby incorporated by reference herein, teaches a package assembly for a surgical mesh including a carrier assembly having a first substantially flat, flexible protective element lying in a first plane and having a periphery, and a second substantially flat, flexible protective element having a periphery and being positioned in a second plane parallel and substantially adjacent to the first plane. The package assembly includes a substantially flat, flexible surgical mesh having first and second sides, whereby the mesh is positioned between the first and second protective elements. The first and second protective elements are further dimensioned to substantially cover the respective first and second sides of the surgical mesh. The first and second protective elements are joined together along at least a portion of their respective peripheries, but along no more of the periphery than that which will allow the first and second protective elements to be separated from one another to allow removal of the mesh by a user without separating the joined portion of their peripheries.

In spite of the above advances, there remains a need for a package for medical devices, such as surgical mesh products, that resists bending, securely holds the mesh in place, and that minimizes required storage space. There also remains a need for a package for medical devices that enables the medical device to remain flat so that, when deployed, the medical device does not have any creases or folds. In addition, there remains a need for a package for a medical device that includes a separate compartment for holding one or more accompanying instruction manuals, packages that may be assembled around the medical device, and packages that may be assembled without using any glue (e.g. a package that uses mechanical interlocking elements such as locking tabs and slits). In addition, there remains a need for a package for medical devices that avoids assembly costs associated with gluing and using double-sided tapes to complete or seal packages, and that provides rigidity with an inner chamber suitable for housing a medical device without exposing the medical device to compressive forces associated with shipping and handling. Moreover, there remains a need for a package for medical devices having a closing flap or cover that enables the package to be closed without damaging the underlying structure of the package or the contents of the package.

There also remains a need for a package for medical devices that has enhanced integrity and functionality so that surgical personnel may easily remove and control the medical device as it is removed from the package. There also remains a need for a package for dispensing medical devices that securely locks so that the medical devices do not easily spill out of the packaging when the package is opened. In addition, there is a need for medical packaging which does not require additional adhesive to secure the packaging and the medical products, thereby reducing the bio-burden and the possibility of adhesive leaching into the medical device. There also remains a need for a medical package dispenser whereby a medical device can be inserted into the package during a folding and/or tucking operation, which allows for easy filling of the package without risking folds or bends in the medical device and without risking the medical device catching a surface of the dispenser package during removal of the medical device from the package. There also remains a need for medical packaging that prevents unwanted drops or mishandling, and that allows for easy access and dispensing of the medical product. There also remains a need for medical packaging whereby the product is covered and protected in a sterile environment until immediately prior to use. Moreover, there remains a need for a package that stores a booklet, such as an instruction manual, that retains the booklet within the package, that physically separates the booklet from a medical device stored in the package, and that enables medical personnel to easily remove the booklet from the package for use during a surgical procedure.

SUMMARY OF THE INVENTION

Surgical mesh products require packaging that enables the mesh to remain flat so that, when deployed, the mesh does not have any creases or folds. The present invention provides a package for medical devices, such as surgical mesh products, that resists bending, securely holds the medical device in place, and minimizes the required storage space for the package.

In one embodiment, a flat box for storing a medical device, such as a surgical mesh, preferably includes a first panel having an upper edge, a lower edge, a first side edge, and a second side edge, and a second panel hingedly connected with the lower edge of the first panel, the second panel being foldable over the first panel for defining a storage compartment. The medical device may be stored in the storage department. In one embodiment, the flat box preferably includes a first side flap hingedly connected with the first side edge of the first panel and being foldable over and interlockable with the second panel for closing a first side of the box, and a second side flap hingedly connected with the second side edge of the first panel and being foldable over and interlockable with the second panel for closing a second side of the box.

In one embodiment, the box preferably includes a cover hingedly connected with the upper edge of the first panel for moving between an open position for providing access to the storage compartment and a closed position for closing the storage compartment. When in the closed position, the cover is preferably folded over and interlocked with the first and second side flaps and the second panel. The structural integrity of the closed box is preferably enhanced by interlocking the cover with the first and second side flaps and the second panel.

In one embodiment, the cover desirably has a free edge including a plurality of locking tabs projecting from the free edge, and each of the first and second side flaps and the second panel desirably includes at least one cover locking slit adapted to receive at least one of the cover locking tabs for mechanically interlocking with the cover so as to hold the cover in the closed position.

In one embodiment, the cover locking tabs at the free edge of the cover define a first arc, and the cover locking slits on the first side flap, the second panel, and the second side flap define a second arc that conforms to the first arc. Although the present invention is not limited by any particular theory of operation, it is believed that matching the first arc of the cover locking tabs with the second arc of the cover locking slits provides for smoother interlocking of the cover with the box and easier unlocking of the cover locking tabs from the associated locking slits without damaging the box. In addition, the matching arcs provide a tighter fit between the cover and the side flaps and second panel.

In one embodiment, the cover locking tabs preferably include first and second central locking tabs and first and second outer locking tabs that are located outside the central locking tabs. In one embodiment, the first and second central locking tabs are hingedly connected with the cover.

In one embodiment, the first outer locking tab on the cover is adapted for being mechanically interlocked with a first cover locking slit on the first side flap, the second outer locking tab on the cover is adapted for being mechanically interlocked with a second cover locking slit on the second side flap, and the first and second central locking tabs on the cover are adapted for being mechanically interlocked with a pair of central cover locking slits on the second panel.

In one embodiment, the first side flap preferably includes at least one locking tab and the second panel preferably includes at least one first side flap locking slit adapted to receive the at least one locking tab on the first side flap for mechanically interlocking the first side flap with the second panel. In one embodiment, the second side flap preferably includes at least one locking tab and the second panel preferably includes at least one second side flap locking slit adapted to receive the at least one locking tab on the second side flap for mechanically interlocking the second side flap with the second panel.

In one embodiment, the at least one first side flap locking slit desirably includes a first locking slit that is parallel to a first side of the second panel and a second locking slit that is angled relative to the first side of the second panel, and the at least one second side locking slit preferably includes a first locking slit that is parallel to a second side of the second panel and a second locking slit that is angled relative to the second side of the second panel. Although the present invention is not limited by any particular theory of operation, it is believed that angling a pair of locking slits relative to one another, a greater locking force may be created between the locking slits and the side locking flaps.

In one embodiment, the first and second central locking tabs are preferably hingedly connected with the cover so as to be more flexibly connected with the cover than the first and second outer locking tabs. Providing flexibly connected central locking tabs on the cover preferably enables easier interlocking of the cover with the box without damaging the structure or tearing the box, and closer and more enhanced locking of the cover with the box.

In one embodiment, the box desirably includes a third panel hingedly connected with a lower edge of the second panel. In one embodiment, the third panel is preferably foldable over the second panel for defining a second storage compartment between the second panel and the third panel. In one embodiment, when the second panel is folded over the first panel, the third panel is preferably adjacent the first panel. In one embodiment, when the third panel is folded over the second panel and the second panel is folded over the first panel, the third panel preferably divides the first storage compartment from the second storage compartment.

In one embodiment, the second panel preferably includes an elongated opening extending between major faces of the second panel that provides an access opening for the second storage compartment. In one embodiment, the elongated opening in the second panel is preferably adapted to hold at least one booklet in the second storage compartment.

In one embodiment, a flat box for storing a flat medical device preferably includes a first panel including an upper edge, a lower edge, a first side edge, and a second side edge, a second panel hingedly connected with the lower edge of the first panel, and a third panel hingedly connected with a lower edge of the second panel. The box desirably includes a first side flap hingedly connected with the first side edge of the first panel and a second side flap hingedly connected with the second side edge of the first panel. In one embodiment, the third panel is preferably foldable over the second panel and the second panel is foldable over the first panel for forming a first storage compartment between the first and third panels and a second storage compartment between the second and third panels. The first side flap is preferably foldable over and interlockable with the second panel for closing a first side of the box, and the second side flap is foldable over and interlockable with the second panel for closing a second side of the box. The box desirably includes a cover hingedly connected with the upper edge of the first panel, whereby the cover is foldable over and interlockable with the first and second side flaps and the second panel for holding the cover in a closed position.

In one embodiment, the flat box is a foldable paperboard blank including the first, second and third panels, the first and second side flaps, and the cover.

In one embodiment, the upper edge of the first panel and an upper edge of the third panel preferably define an opening for the first storage compartment, and the second panel preferably has an elongated opening formed therein defining an opening for the second storage compartment.

In one embodiment, the second panel desirably includes at least one first side flap locking slit adapted to receive at least one locking tab on the first side flap for mechanically interlocking the first side flap with the second panel, and at least one second side flap locking slit adapted to receive at least one locking tab on the second side flap for mechanically interlocking the second side flap with the second panel.

In one embodiment, each of the first and second side flaps and the second panel preferably includes at least one cover locking slit adapted to receive a respective locking tab on the cover for mechanically interlocking the cover with the first and second side flaps and the second panel for holding the cover in the closed position.

In one embodiment, the cover preferably includes first and second central locking tabs adapted to mechanically interlock with a pair of central cover locking slits on the second panel, a first outer locking tab adapted to mechanically interlock with a cover locking slit on the first side flap and a second outer locking tab adapted to mechanically interlock with a cover locking slit on the second side flap. The cover locking tabs preferably define a first arc and the cover locking slits on the first side flap, the second panel, and the second side flap preferably define a second arc that substantially matches the contour of the first arc. Matching the arcs of the locking tabs with the locking slits desirably enables closer locking of the cover with the box and easier closing and opening of the cover that avoid tearing or damaging the box.

In one embodiment, a flat box for storing a surgical mesh may include a first panel having an upper edge, a lower edge, a first side edge, and a second side edge, a second panel hingedly connected with the lower edge of the first panel, and a third panel hingedly connected with a lower edge of the second panel. The box desirably includes a first side flap hingedly connected with the first side edge of the first panel, and a second side flap hingedly connected with the second side edge of the first panel. In one embodiment, the third panel is desirably foldable over the second panel and the second panel is foldable over the first panel for forming a first storage compartment between the first and third panels and a second storage compartment between the second and third panels. A surgical mesh is preferably stored in the first storage compartment, and at least one booklet is preferably stored in the second storage compartment. In one embodiment, the first side flap is desirably foldable over and interlockable with the second panel for closing a first side of the box and for holding the second and third panels against the first panel, and the second side flap is foldable over and interlockable with the second panel for closing a second side of the box and for holding the second and third panels against the first panel. The box desirably includes a cover hingedly connected with the upper edge of the first panel. The cover is preferably foldable over and interlockable with the first and second side flaps and the second panel for holding the cover in a closed position so as to cover the surgical mesh and the at least one booklet.

In one embodiment, a box or package for a medical device is flat, which reduces storage space, provides rigid support for the medical device, and prevents the medical device from shifting within the assembled box.

In one embodiment, the box is assembled and sealed by folding the parts of the box into a flat structure and interlocking the parts using only locking tabs and locking slits that are provided on the parts. The above-described box minimizes assembly costs associated with gluing and/or using double-sided tapes to assemble or close packages.

In one embodiment, the package or box includes a foldable blank that may be assembled around the medical device stored therein. The box preferably provides rigidity and an inner storage chamber suitable for housing a medical device without exposing the device to compressive forces associated with shipping and handling.

In one embodiment, the box or package may include a rounded cover or closing flap with rounded locking tabs projecting therefrom to enable the box to be closed without damaging or tearing the box, such as a box made of paperboard. In one embodiment, at least some of the locking tabs have scores or fold lines that facilitate locking of a flat box, especially for embodiments made of heavy-gauge paperboard.

In one embodiment, the box has a separate storage compartment for printed materials, which provides a low-profile structure that includes written materials or booklets for end-users. Providing a storage chamber for printed materials also increases the box's resistance to bending.

These and other preferred embodiments of the present invention will be described in more detail below.

BRIEF DESCRIPTION OF THE DRAWING

FIG. 1 shows a top plan view of a foldable blank for a box for a medical device, in accordance with embodiment of the present invention.

DETAILED DESCRIPTION

Figure 2A:
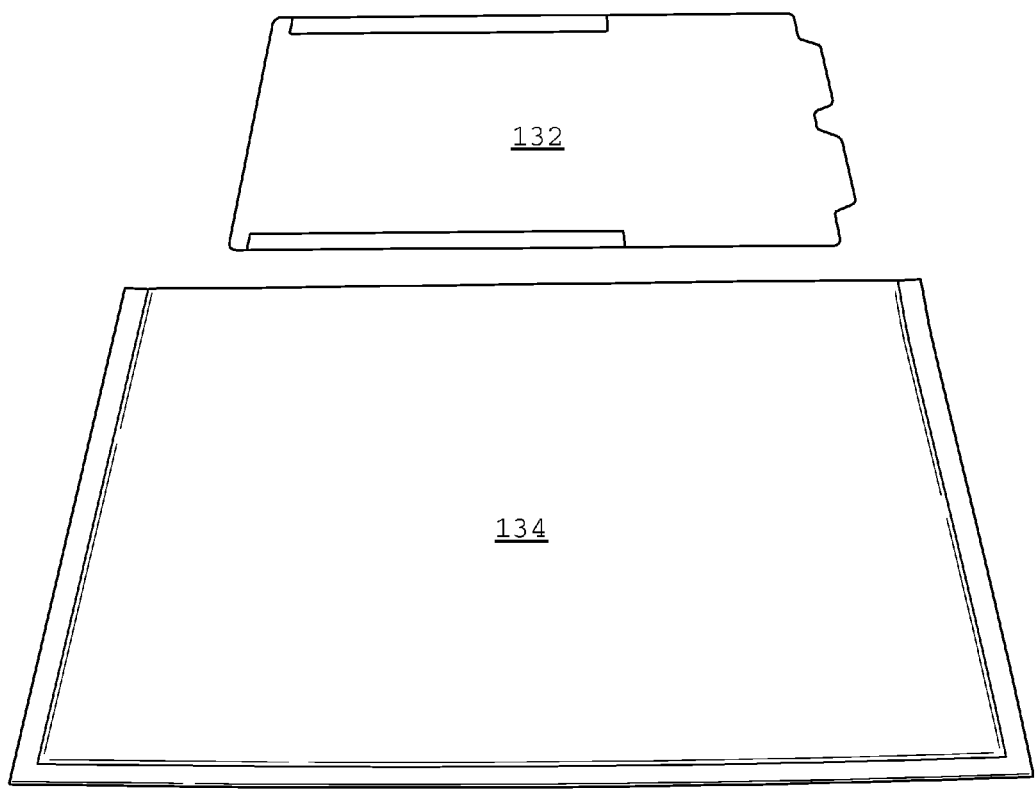
FIGS. 2A-2C show a method of loading a folder containing a medical device into a sealable pouch, in accordance with one embodiment of the present invention.

Referring to FIG. 1, in one embodiment, a box 20 for holding a medical device, such as a surgical mesh, preferably includes a foldable blank 22 having a first panel 24 with an upper edge 26, a lower edge 28, a first side edge 30, and a second side edge 32. The first panel 24 preferably has a height $H_1$ of about 20-50 cm, and a width $W_1$ of about 20-50 cm. In one embodiment, the foldable blank 22 is preferably made of a rugged cellulose material such as paperboard. The paperboard blank may have fold lines that enable the various parts of the blank to be folded over one another for assembling the blank 22 into a flat box. The paperboard blank may be made of lighter and heavier gauge materials. In one embodiment, the paperboard blank has a gauge of about 18-30 pt., and more preferably about 24 pt. (i.e. 0.0024").

In one embodiment, the foldable blank 22 preferably includes a cover 34 having a lower edge 36 that is hingedly connected with the upper edge 26 of the first panel 24 along a first fold line 38. In one embodiment, the cover 34 preferably includes an outer perimeter 40 that defines a first arc or rounded surface. The cover 34 preferably includes a cover opening tab 42 that may be engaged for opening the cover 34. The cover 34 desirably includes a pair of central locking tabs 44A, 44B that project from the outer perimeter 40 on opposite sides of the cover opening tab 42. Each of the first and second central locking tabs 44A, 44B is hingedly connected to the cover 34. In one embodiment, the first central locking tab 44A is hingedly connected with the cover 34 along a second fold line 46, and the second central locking tab 44B is hingedly connected with the cover 34 along a third fold line 48. In one embodiment, the cover 34 desirably includes first and second outer locking tabs 50A, 50B that are located outside the respective first and second central locking tabs 44A, 44B. In one embodiment, the cover opening tab 24, the first and second central locking tabs 44A, 44B, and the first and second outer locking tabs 50A, 50B have curved outer perimeters. The central opening tab 42, the central locking tabs 44A, 44B and the outer locking tabs 50A, 50B are spaced from one another about the outer perimeter 40 of the cover 34.

As noted above, in one embodiment, the first and second central locking tabs 44A, 44B are hingedly connected to the cover 34 via respective fold lines 46, 48. In contrast, the outer locking tabs 50A, 50B are not hingedly connected with the cover 34 so that there is no fold line between the first and second outer locking tabs 50A, 50B and the cover 34. Although the present invention is not limited by any particular theory of operation, it is believed that hingedly connecting the first and second central locking tabs 44A, 44B to the cover 34 will facilitate easier locking the cover in a closed position and opening and closing the cover without damaging any portion of the cover or the locking tabs. The absence of fold lines in conjunction with the first and second outer locking tabs 50A, 50B is believed to provide more rigidity in that area of the cover 34 for providing a more secure locking force and a more rigid package when the cover 34 is in a closed position.

In one embodiment, the foldable blank 22 desirably includes a first side flap 52 that is hingedly connected with the first side edge 30 of the first panel 24 along a fourth fold line 54. The first side flap 52 preferably includes an upper end having a concave surface 56, an intermediate section having a substantially vertically-extending edge 58, and a lower end including an angled edge 60 that tapers inwardly between the vertical edge 58 and the first side edge 30 of the first panel 24. In one embodiment, the first side flap 52 desirably includes an upper first side flap locking tab 62 and a lower first side flap locking tab 64. The first side locking flap also desirably includes a cover locking slit 66 that is adapted to receive the first outer locking tab 50A on the cover 34 for mechanically interlocking the cover with the first side flap.

In one embodiment, the foldable blank 22 desirably includes a second side flap 68 that is hingedly connected with the second side edge 32 of the first panel 24 along a fifth fold line 70 extending between the first panel 24 and the second side flap 68. In one embodiment, the second side flap 68 desirably includes an upper end including a concave edge 72, an intermediate section including a vertically extending edge 74 that is substantially parallel with the second side edge 32 of the first panel 24, and a lower end including a sloping surface 76 that tapers inwardly between the vertical edge 74 and the second edge 32 of the first panel 24. The second side flap 68 desirably includes an upper second side flap locking tab 78 and a lower second side flap locking tab 80. The second side flap 68 desirably includes a cover locking slit 82 that is adapted to receive the second outer locking tab 50B on the cover 34 for mechanically interlocking the cover with the second side locking flap.

In one embodiment, the foldable blank 22 desirably includes a second panel 84 having an upper edge 86, a lower edge 90, a first side edge 92, and a second side edge 94. The upper edge 86 of the second panel 84 is preferably hingedly connected with the lower edge 28 of the first panel 24 along a sixth fold line 88. The second panel 84 preferably has a height $H_2$ of approximately 20-50 cm and a width $W_2$ of approximately 20-50 cm. The first and second side edges 92, 94 of the second panel 84 preferably have cutouts 96A, 96B so that the width $W_2$ of the second panel 84, adjacent the lower edge 90 thereof, is slightly less than the width $W_1$ of the first panel 24. The cutouts 96A, 96B preferably provide space for more efficient and compact folding of the panels and side flaps 52, 68 of the blank 22 when assembling the box 20. In one embodiment, the second panel 84 has an outer perimeter that is smaller than the outer perimeter of the first panel 24 so that the second panel fits entirely within the boundary of the first panel when folded over the first panel.

In one embodiment, the second panel 84 preferably includes a first locking slit 98 adapted to receive the upper locking tab 62 on the first side flap 52, and a second locking slit 100 adapted to receive the lower locking tab 64 on the first side flap 52. The second panel 84 desirably includes a first locking slit 102 adapted to receive the upper locking tab 78 on the second side flap 68, and a second locking slit 104 adapted to receive the lower locking tab 80 on the second side flap 68. The second panel 84 desirably includes a pair of cover locking slits 106A, 106B that are adapted to receive the respective first and second central locking tabs 44A, 44B on the cover 34. The first and second cover locking slits 106A, 106B preferably extend along respective axes that are angled relative to the lower edge 90 of the second panel 84. The second panel 84 also desirably includes an elongated opening 108 that defines an opening to a storage compartment adapted to receive one or more booklets, such as an instruction manual, as will be described in more detail herein.

In one embodiment, the blank 22 for the flat box 20 desirably includes a third panel 110 having a foldable upper edge 112, a lower edge 114, a first side edge 116, and a second side edge 118. In one embodiment, the upper edge 112 of the third panel 110 is hingedly connected with the lower edge 90 of the second panel 84 via a seventh fold line 120. The third panel 110 desirably has a height $H_3$ of approximately 20-50 cm and a width $W_3$ of approximately 20-50 cm. In one embodiment, the height $H_3$ of the third panel 110 is slightly less than the height $H_2$ of the second panel 84. In one embodiment, the width $W_3$ of the third panel 110 is approximately equal to the width $W_2$ of the second panel 84. In one embodiment, the third panel preferably defines an area that is smaller than the second panel, which, in turn, covers an area that is smaller than the first panel.

Figure 2B:
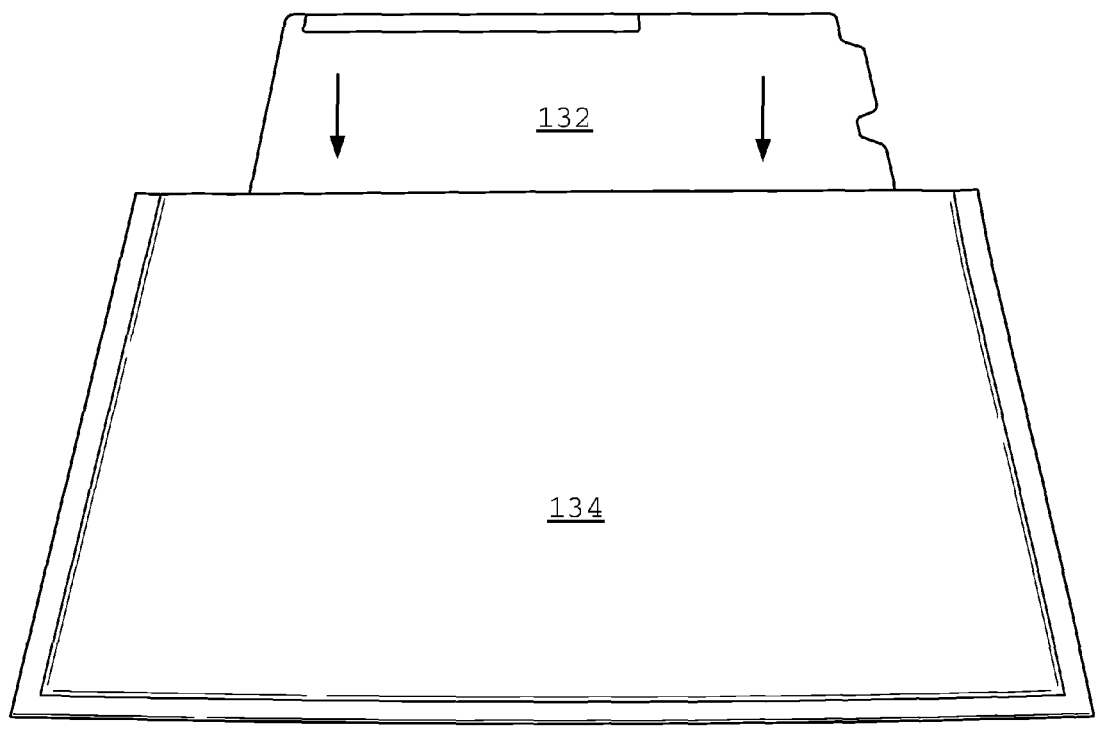
Figure 2C:
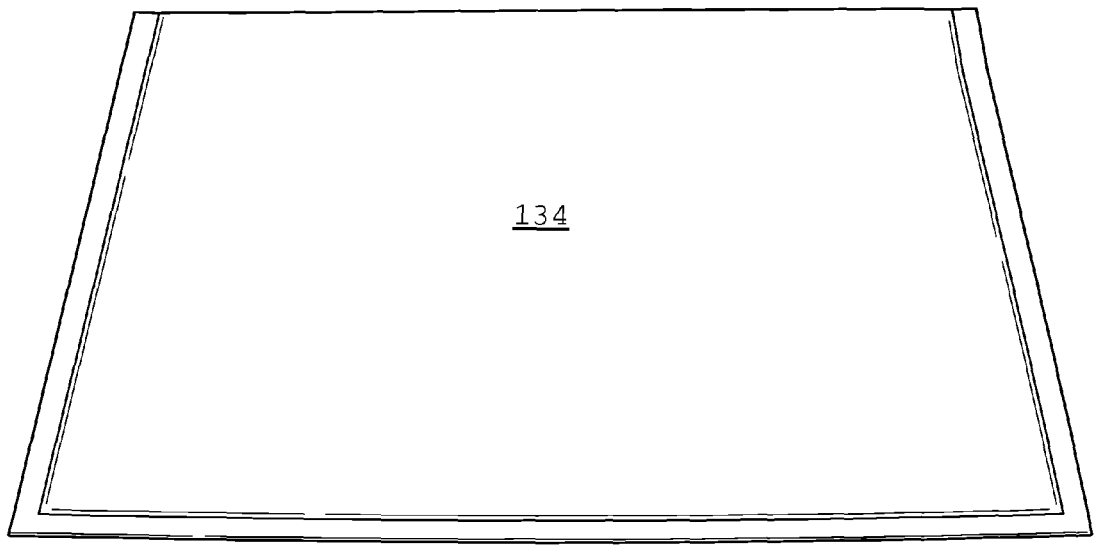

Referring to FIG. 2A, in one embodiment, the foldable blank 22 shown in FIG. 1 is adapted to receive a medical device, preferably positioned over the first panel 24. In one embodiment, the medical device is a surgical mesh (not shown) that is stored within a folder 132, which, in turn, is stored within a sealable pouch 134. In one embodiment, the surgical mesh is substantially flat, as described in commonly assigned U.S. patent application Ser. No. 12/815,275, filed Jun. 14, 2010, the disclosure of which is hereby incorporated by reference herein. FIG. 2B shows the folder 132 containing the surgical mesh being inserted into the sealable pouch 134. The folder may be the two component folder disclosed in commonly assigned U.S. patent application Ser. No. 12/820, 344, filed Jun. 22, 2010, the disclosure of which is hereby incorporated by reference herein. FIG. 2C shows the sealable pouch 134 after the folder 132 (FIG. 2B) containing the surgical mesh has been fully inserted into the pouch 134. The pouch may be sealed so that the mesh and the folder are completely sealed inside the pouch, as disclosed in commonly assigned U.S. patent application Ser. No. 820,401, filed Jun. 22, 2010, the disclosure of which is hereby incorporated by reference herein.

Figure 3:
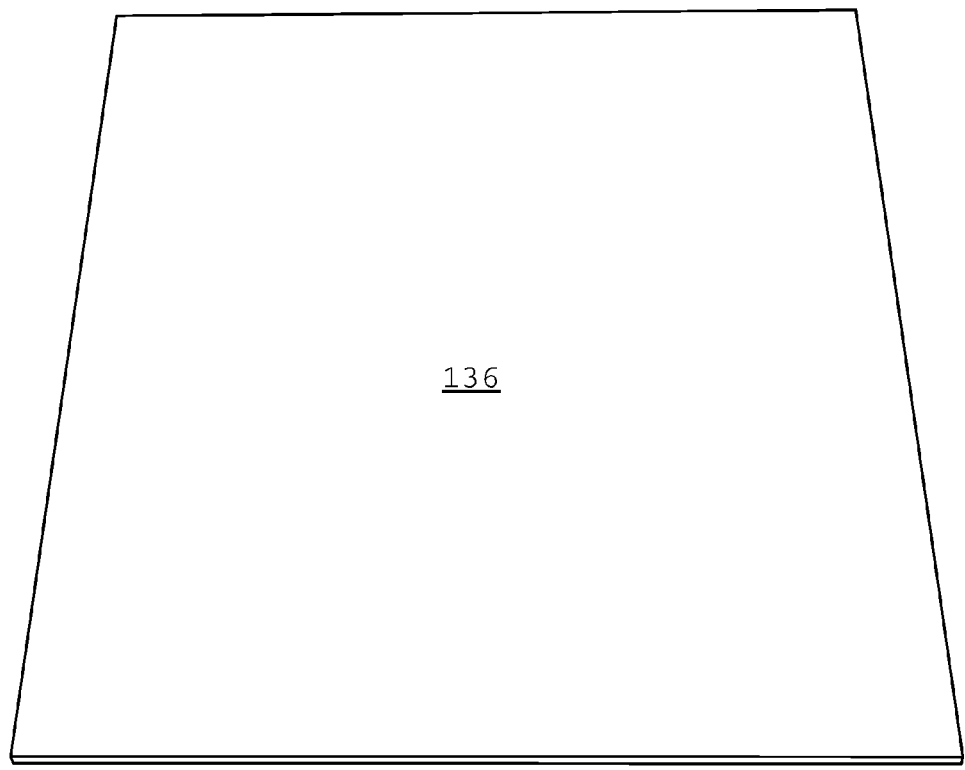
FIG. 3 shows a booklet insertable into a storage compartment of a box for a medical device, in accordance with one embodiment of the present invention.

Referring to FIG. 3, in one embodiment, the elongated opening 108 (FIG. 1) provided on the second panel 84 is preferably adapted to receive a booklet 136, such as an instruction manual, that provides surgical instructions for properly using the medical device stored in the sealed pouch 134 (FIG. 2C).

Figure 4A:
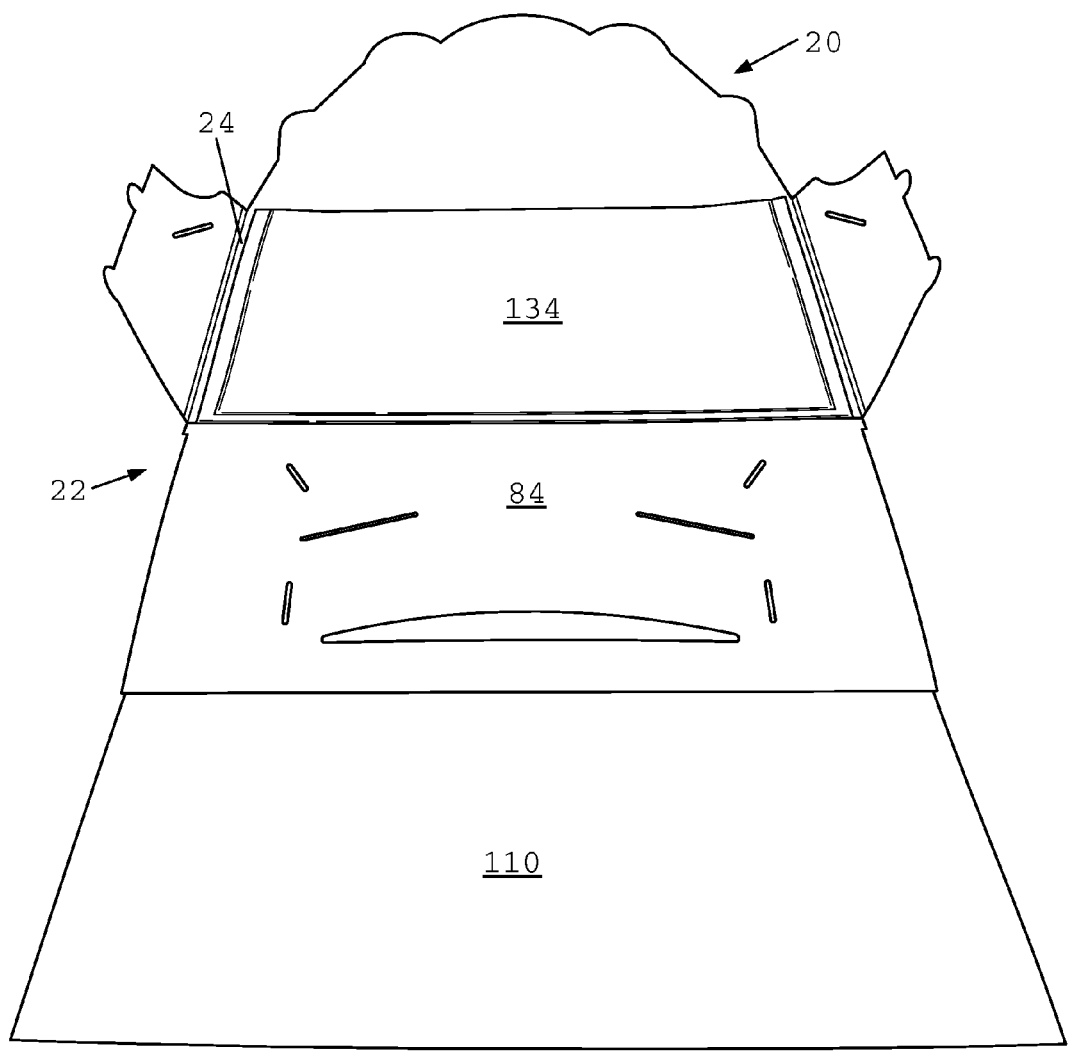
FIGS. 4A-4G show a method of assembling a box around a medical device, in accordance with one embodiment of the present invention.
Figure 4B:
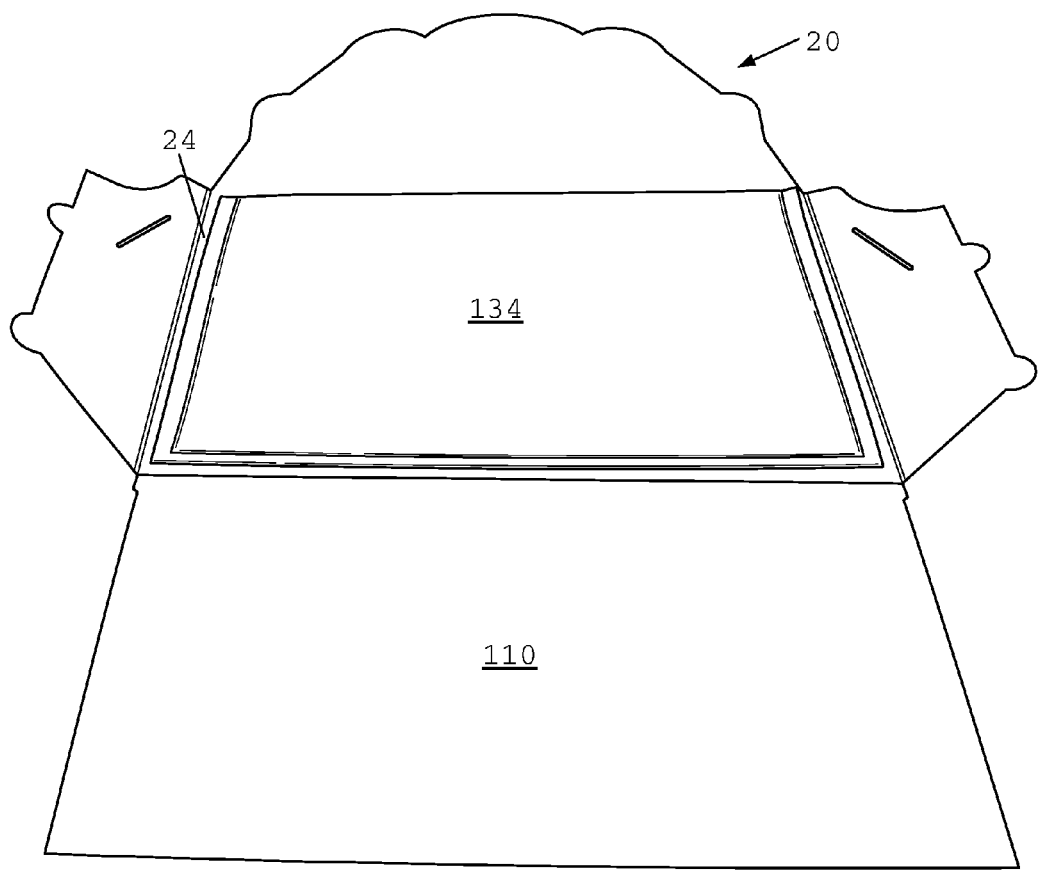

Referring to FIG. 4A, in one embodiment, the sealed pouch 134, having the medical device sealed therein is desirably positioned over a central region of the first panel 24 of the blank 22. Referring to FIGS. 4A and 4B, in one embodiment, in order to assemble the box 20 around the sealed pouch 134, the third panel 110 of the blank 22 is folded over the second panel 84 of the blank.

Figure 4C:
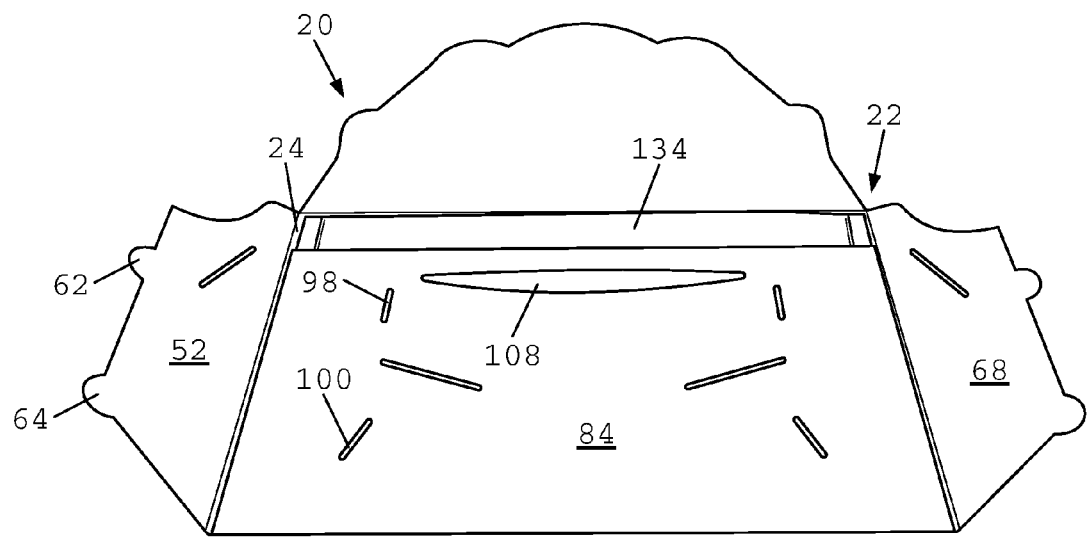

Referring to FIGS. 4B and 4C, in one embodiment, the second panel 84 may be folded over the first panel 24 to form a first storage compartment adapted to contain the sealed pouch 134. When the second panel 84 is folded over the first panel 24, the sealed pouch 134 preferably lays within the first storage compartment between the first panel 24 and the third panel 110 (FIGS. 4A and 4B). The box 20 also desirably includes a second storage compartment disposed between the third blank 110 and the second blank 84 (FIG. 4A). Access to the second storage compartment is through the elongated opening 108 formed in the second panel 84. Once the second panel 84 has been folded over the first panel 24, the first and second side flaps 52, 68 may be folded over the sides of the second panel 84 for closing and locking the sides of the box 20.

Figure 4D:
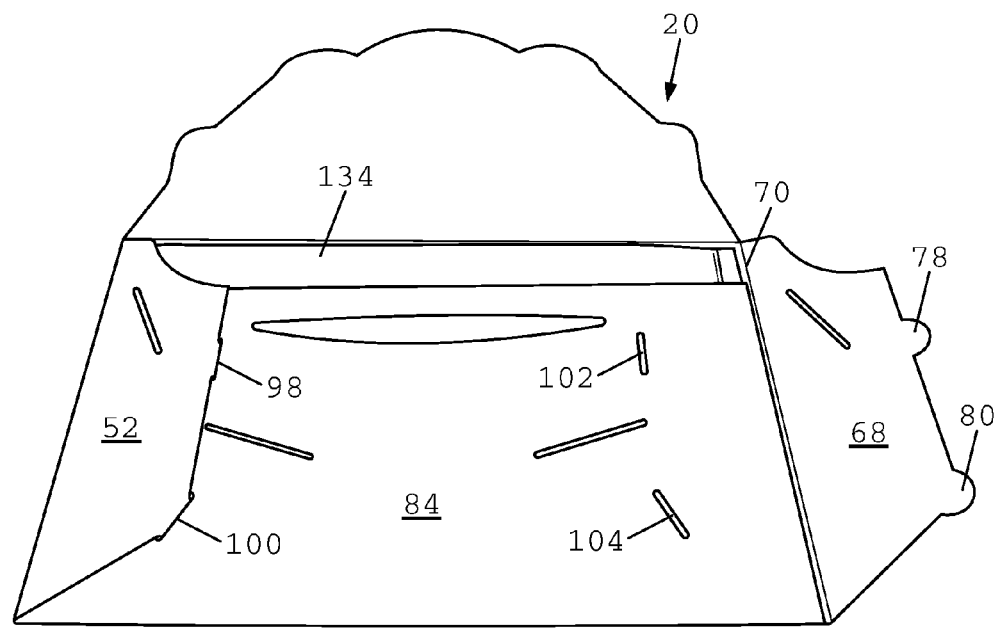

Referring to FIGS. 4C and 4D, in one embodiment, the first side flap 52 is folded over the second panel 84 along the fourth fold line 54 so that the upper locking tab 62 is aligned with the first locking slit 98 and the lower locking tab 64 is aligned with the second locking slit 100. The upper locking tab 62 is preferably inserted into the first locking slit 98 and the lower locking tab 64 is preferably inserted into the second locking slit 100 for mechanically interlocking the first side flap 52 with the second panel 84 in a closed position as shown in FIG. 4D.

Figure 4E:
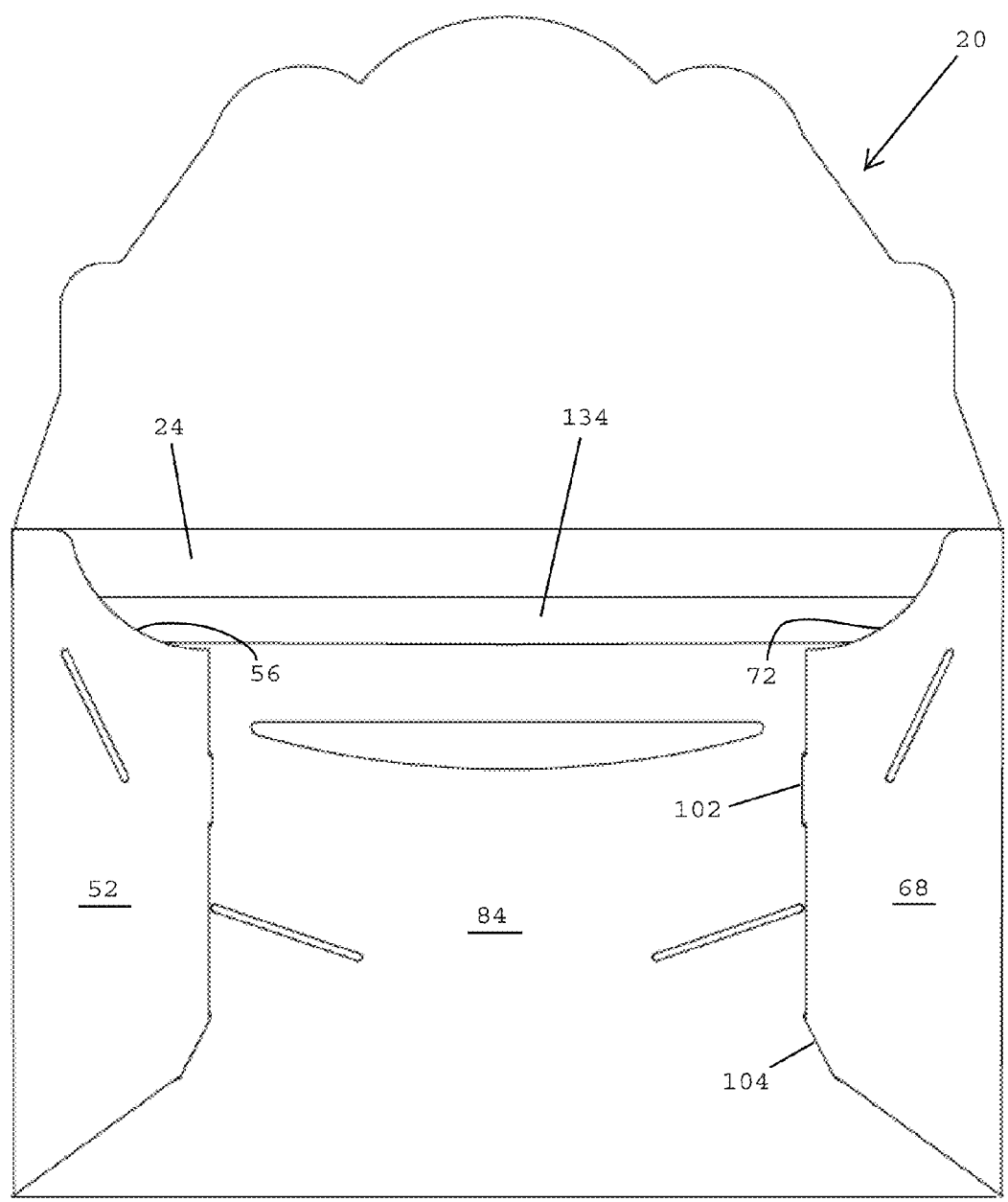

Referring to FIGS. 4D and 4E, in one embodiment, the second side flap 68 is preferably folded over the second panel 84 along the fifth fold line 70 for covering and locking the second side of the box 20. As the second side flap 68 is folded over the second panel 84, the upper locking tab 78 on the second side flap is preferably aligned with the first locking slit 102 and the lower locking tab 80 on the second side flap is preferably aligned with the second locking slit 104. The upper locking tab 78 is preferably inserted into the first locking slit 102 and the lower locking tab 80 is preferably inserted into the second locking slit 104 for closing the second side flap 68 over the second side of the box 20 and mechanically interlocking the second side flap 68 with the second panel 84.

After the first and second side flaps 52, 68 have been closed over the respective first and second sides of the box 20, the sealed pouch 134 containing the mesh implant is preferably disposed within the first storage compartment located between the first panel 24 and the third panel 110 (FIG. 4A) of the blank 22. Referring to FIG. 4E, the concave surfaces 56, 72 on the respective first and second side flaps 52, 68 desirably provide access to the sealed pouch 134. The concave edges 56, 72 also preferably minimize the amount of material between the cover 34 and the second panel 84 so as to reduce the overall thickness of the box 20 when the cover 34 is closed over the second panel 84 for closing the top of the box 20.

Figure 4F:
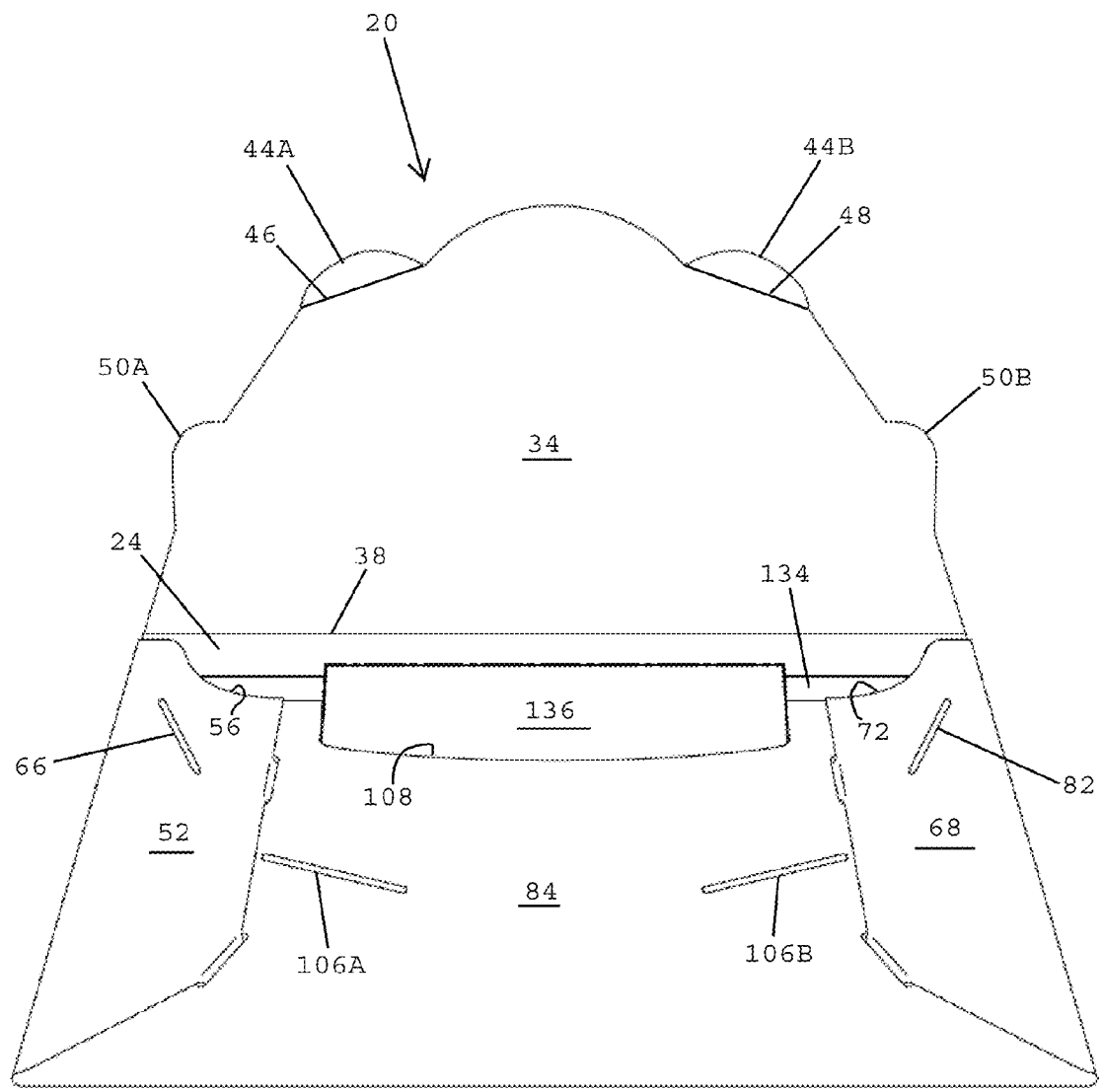

Referring to FIG. 4F, in one embodiment, a booklet 136, such as an instruction manual, may be inserted into the elongated pocket opening 108, with the lower end of the instruction manual 136 preferably disposed in the second storage compartment located between the second panel 84 and the third panel 110 (FIG. 4A) of the blank. As such, the third panel 110 preferably separates the instruction manual 136 from the sealed pouch 134 disposed within the first compartment.

Figure 4G:
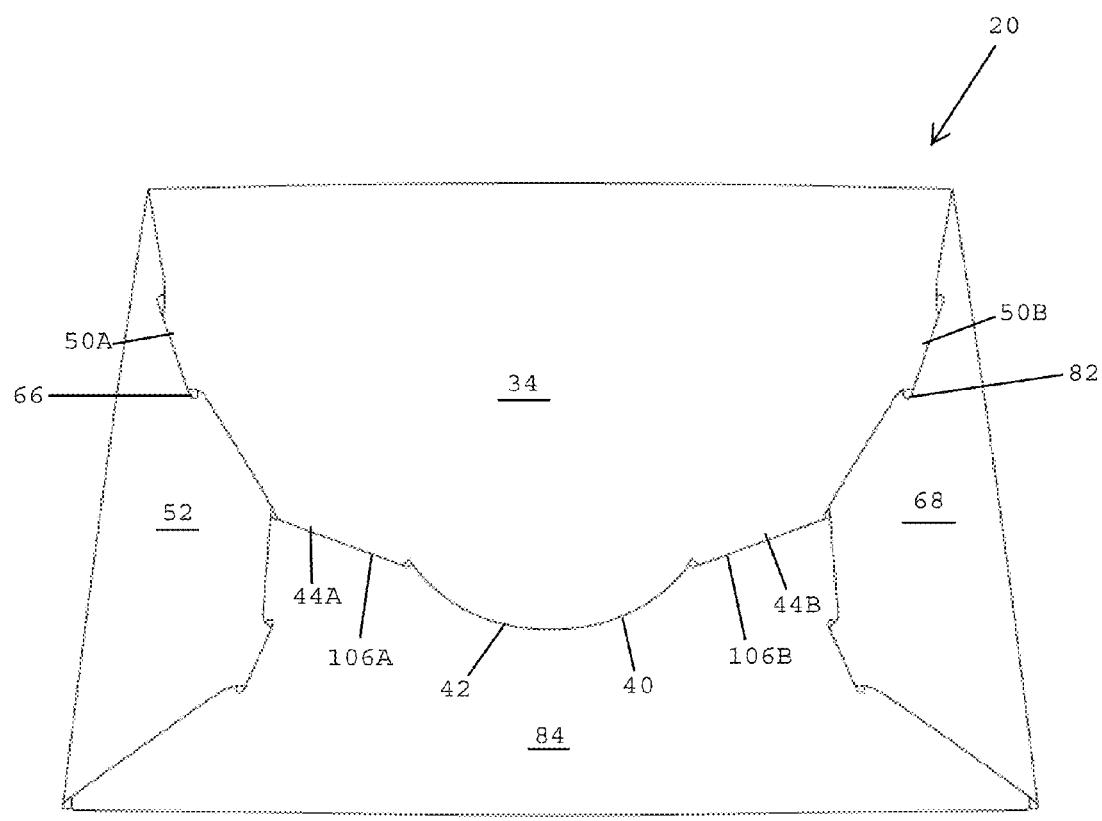

Referring to FIGS. 4F and 4G, in one embodiment, the cover 34 is preferably folded over both the second panel 84 and the first and second side flaps 52, 68 for closing the box 20. In one embodiment, the cover 34 preferably folds along the first fold line 38 extending between the cover 34 and the first panel 24. As the cover 34 is folded, the first outer locking tab 50A is desirably aligned with the cover locking slit 66 on the first side flap 52 and the second outer locking tab 50B is desirably aligned with the cover locking slit 82 on the second side flap 68. In addition, the first central locking tab 44A is aligned with the first central cover locking slit 106A and the second central locking tab 44B is aligned with the second central cover locking slit 106B.

FIG. 4G shows the cover 34 in a closed and locked position with the first outer locking tab 50A inserted into the locking slit 66 on the first side flap 52 and the second outer locking tab 50B inserted into the locking slit 82 on the second side flap 68. In addition, the first central locking tab 44A is inserted into the first central cover locking slit 106A on the second panel 84 and the second central locking tab 44B is inserted into the second central cover slit 106B on the second panel. The second and third fold lines 46, 48 provided on the respective first and second central locking tabs 44A, 44B desirably enable the locking tabs to more easily fit within the respective central cover locking slits 106A, 106B without tearing or permanently deforming the cover 34.

Referring to FIGS. 4F and 4G, in one embodiment, the locking tabs 44A, 44B, 50A, and 50B along the peripheral edge 40 of the cover 34 generally define a first arc extending around the peripheral edge 40 of the cover. The cover locking slits 66, 106A, 106B and 82 on the side flaps 52, 68 and second panel 84 preferably define a second arc that substantially matches the first arc defined by the cover locking tabs. Although the present invention is not limited by any particular theory of operation, it is believed that providing the locking slits in a second arc that substantially conforms to the first arc of the cover locking tabs results in tighter closing of the cover 34 over the second panel 84 and side flaps, and minimizes the likelihood of damaging the cover 34 or the locking tabs during closing and opening of the box. Referring to FIG. 4G, in one embodiment, after the cover 34 is closed over the second panel 84 and the side flaps 52, 68, the cover opening tab 42 desirably overlies a surface of the second panel 84.

Figure 5A:
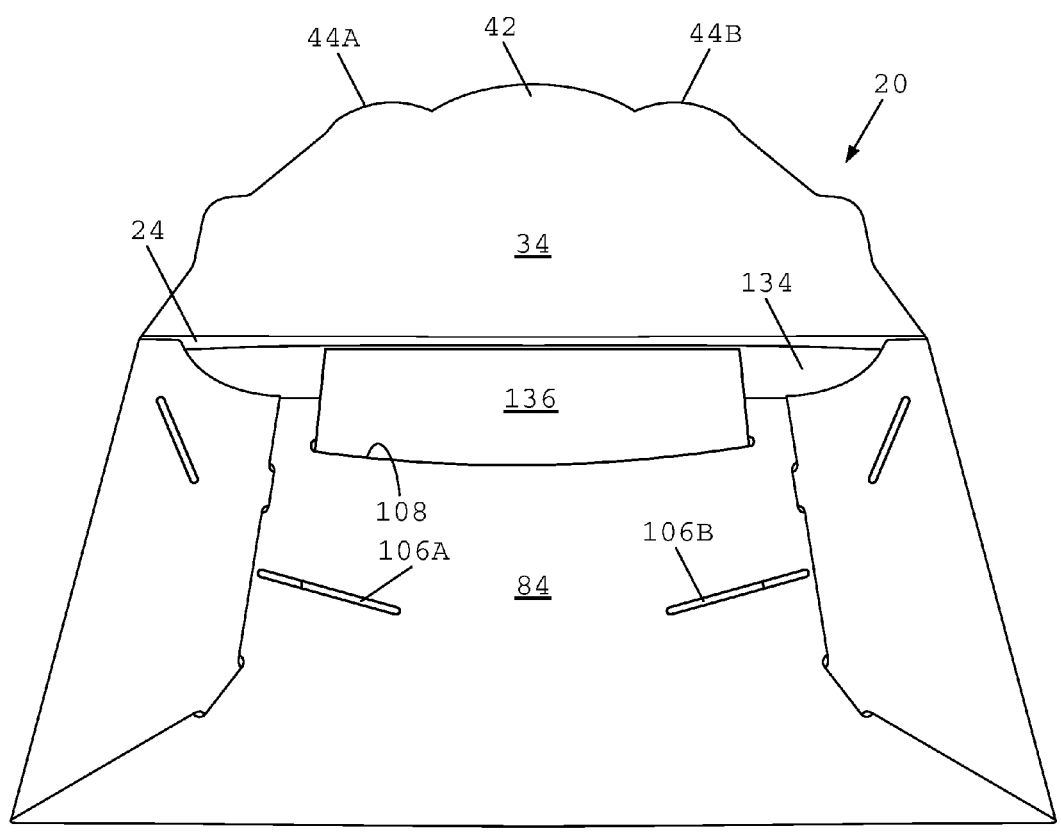
FIGS. 5A-5C show a method of opening a box for accessing an instruction manual and a medical device stored in the box, in accordance with one embodiment of the present invention.

Referring to FIGS. 4G and 5A, in one embodiment, the box 20 is provided to medical personnel during a surgical procedure. The cover 34 may be opened by grasping the cover opening tab 42 so as to unfold the cover relative to the second panel 84. As the cover is pulled away from the second panel 84, the central locking tabs 44A, 44B on the cover 34 may flex as they are retracted from the opposing locking slits 106A, 106B on the second panel 84. Referring to FIG. 5A, when the cover 34 has been opened, the instruction manual 136 desirably projects from the pocket opening 108 and the sealed pouch 134 is accessible between the third panel 110 and the first panel 24 of the blank (FIG. 1).

Figure 5B:
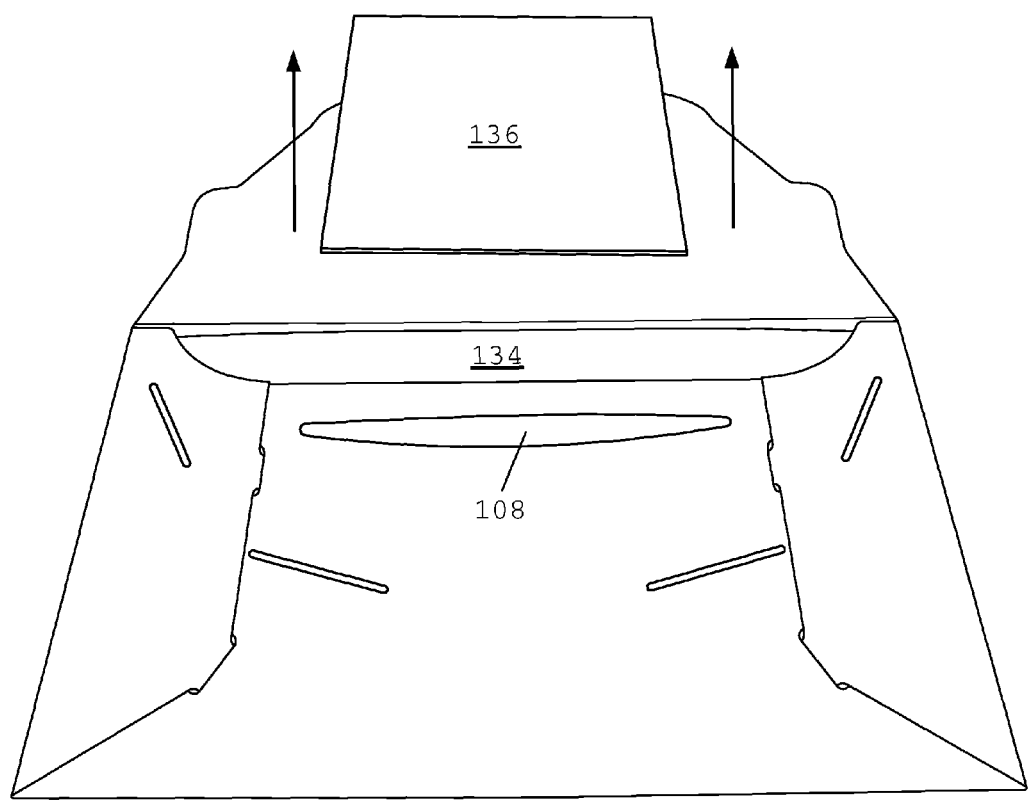

Referring to FIG. 5B, in one embodiment, the instruction manual 136 may be removed from the pocket opening 108 for use by medical personnel. The instructions manual preferably includes instructions for using the medical device stored in the pouch 134.

Figure 5C:
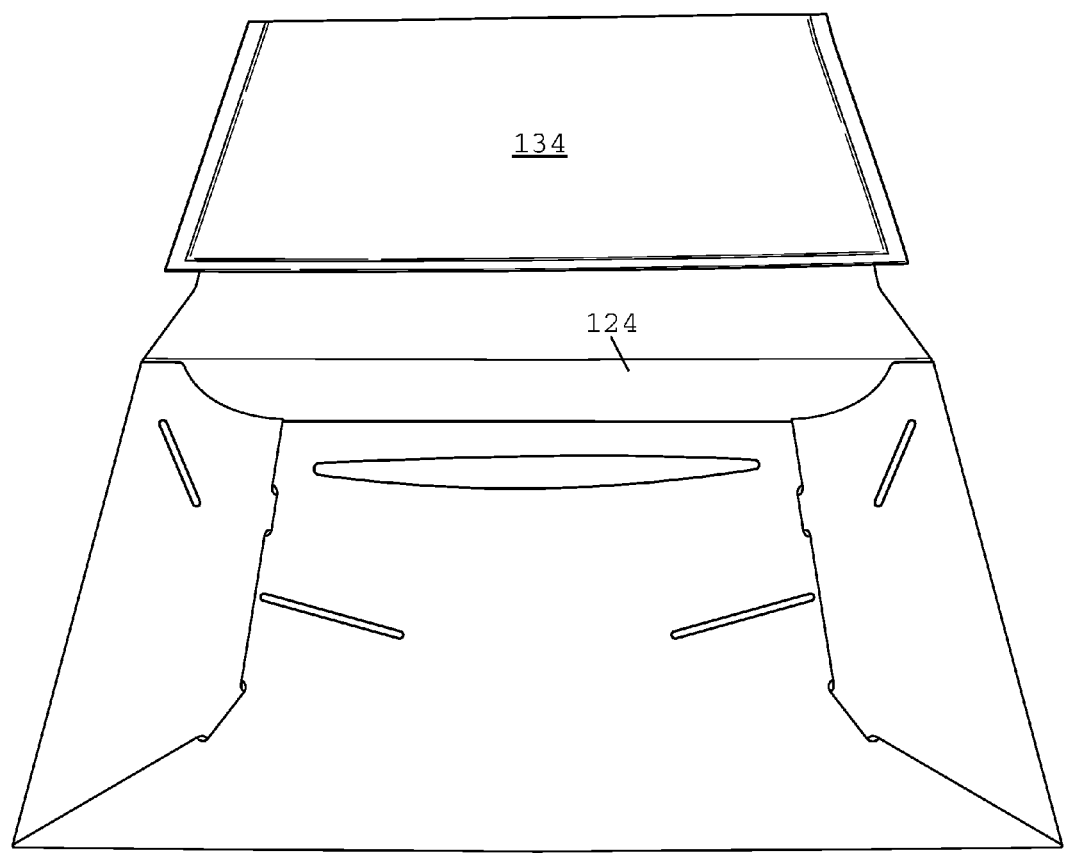

Referring to FIGS. 5B and 5C, after the instruction manual 136 has been removed, the sealed pouch 134 may be removed from the first compartment that is disposed between the third panel 110 and the first panel 124 (FIG. 4A).

Figure 6:
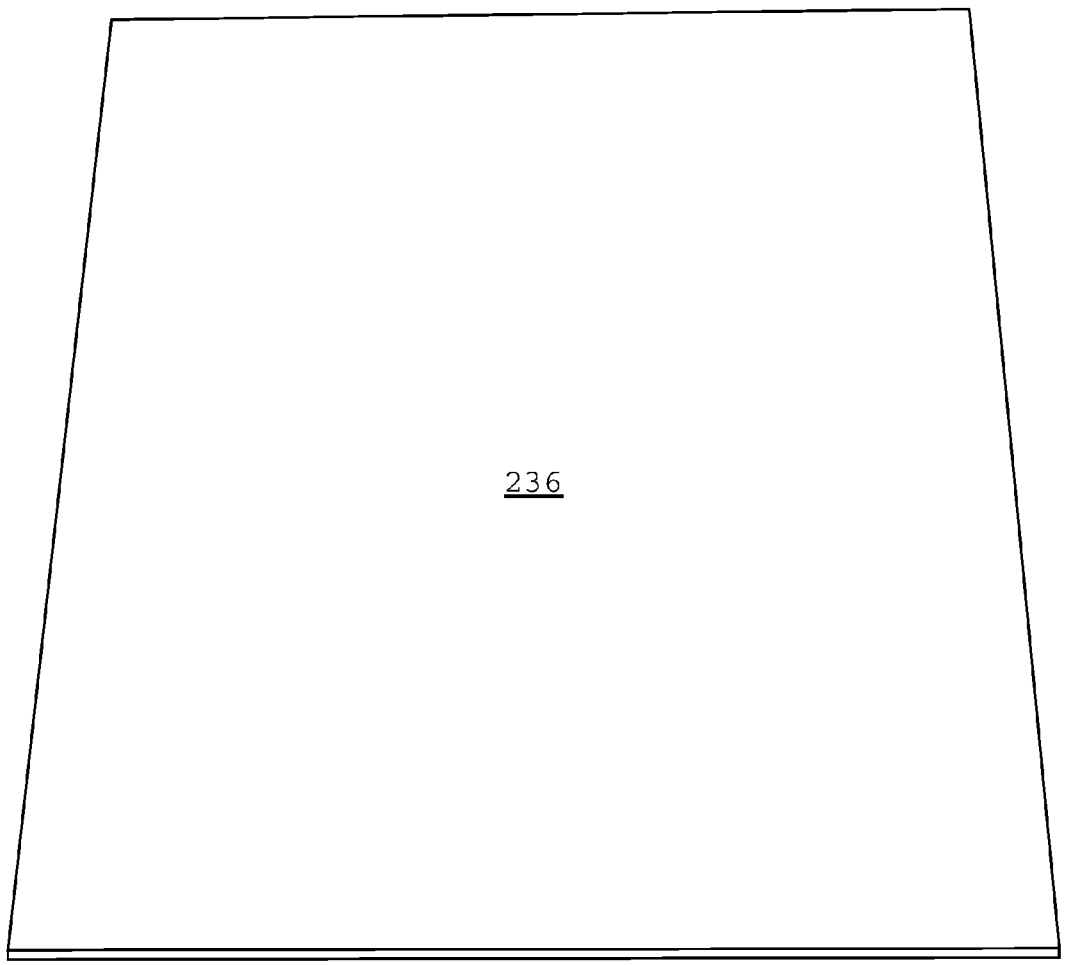
FIG. 6 shows a booklet insertable into a storage compartment of a box for a medical device, in accordance with one embodiment of the present invention.

Referring to FIG. 6, in one embodiment, a booklet 236 having larger dimensions than the booklet 136 shown in FIG. 3 is required. The booklet may be an instruction manual that provides surgical instructions for using the medical device stored in the box. In one embodiment, the booklet 236 may be too large for insertion into the box in a portrait orientation. As such, the instruction manual 236 is desirably oriented in a landscape configuration for insertion and storage in the box.

Figure 7A:
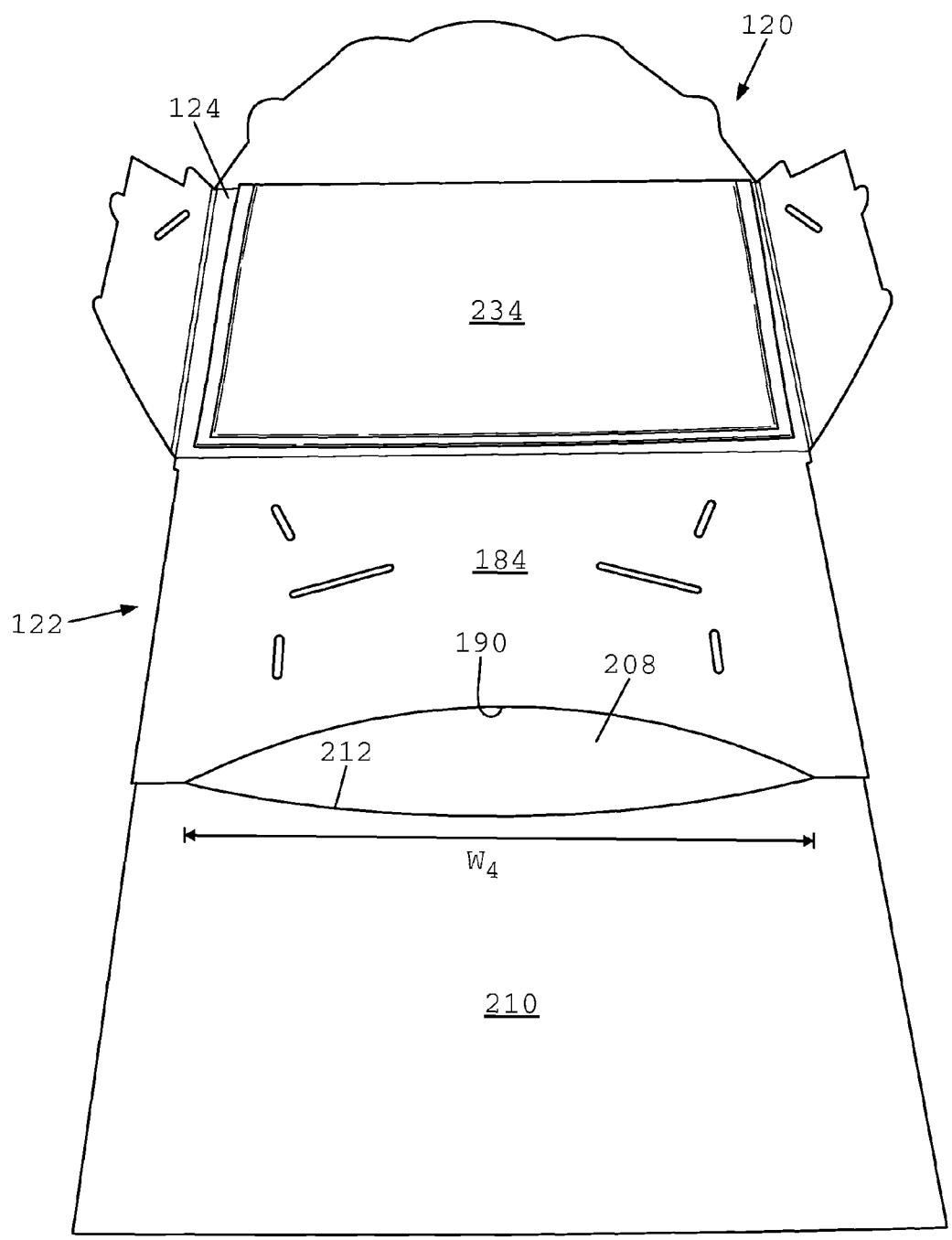
FIGS. 7A-7G show a method of assembling a box for a medical device, in accordance with one embodiment of the present invention.

Referring to FIG. 7A, in one embodiment, an outer box 120 for a medical device is generally similar to the outer box 20 shown and described in FIG. 1. The outer box 120 preferably includes a foldable blank 122 having a first panel 124, a second panel 184, and a third panel 210. An elongated opening 208 preferably extends between the lower edge 190 of the second panel 184 and the upper edge 212 of the third panel 210. The elongated opening 208 preferably has a width $W_4$ that is large enough to receive the booklet 236 (FIG. 6) when the booklet is inserted into the box 120 in a landscape orientation.

Figure 7B:
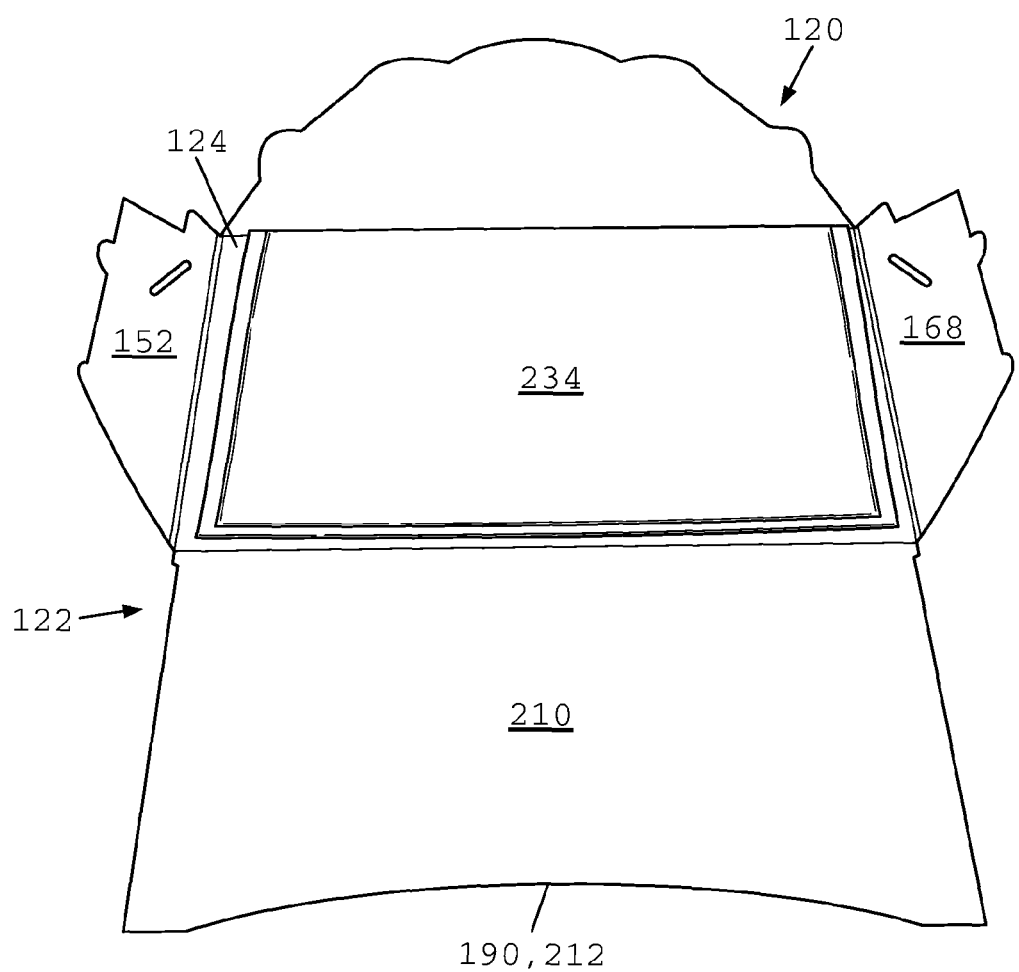

In one embodiment, a sealed pouch 234 containing a medical device, such as a surgical mesh, 2 sealed therein (FIG. 2C) is desirably positioned over a central region of the first panel 124 of the blank 122. The outer perimeter of the first panel is desirably slightly larger than the outer perimeter of the sealed pouch 234. Referring to FIGS. 7A and 7B, in one embodiment, the third panel 210 of the blank is folded over the second panel 184 of the blank so that the lower edge 190 of the second panel 184 is aligned with the upper edge 212 of the third panel 210 (not shown).

Figure 7C:
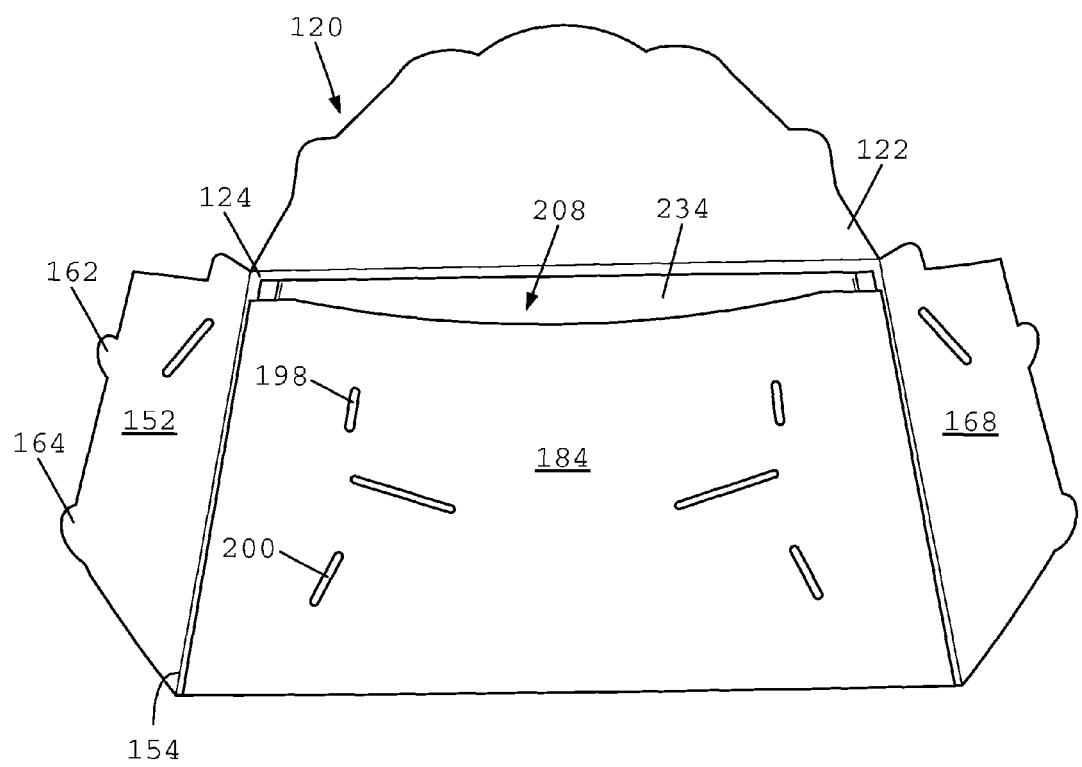

Referring to FIGS. 7B and 7C, in one embodiment, the second panel 184 may be folded over the first panel 124 to form a first storage compartment adapted to contain the sealed pouch 234. When the second panel 184 is folded over the first panel 124, the sealed pouch 234 preferably lays within the first storage compartment between the first panel 124 and the third panel 210 (FIGS. 7A and 7B). The box 120 also desirably includes a second storage compartment disposed between the third panel 210 and the second panel 188. Access to the second storage compartment is through the elongated opening 208 extending between the second and third panels 184, 210. Once the second panel 184 has been folded over the first panel 124, the first and second side flaps 152, 168 may be folded over the sides of the blank 122 for closing and locking the sides of the box 120.

Figure 7D:
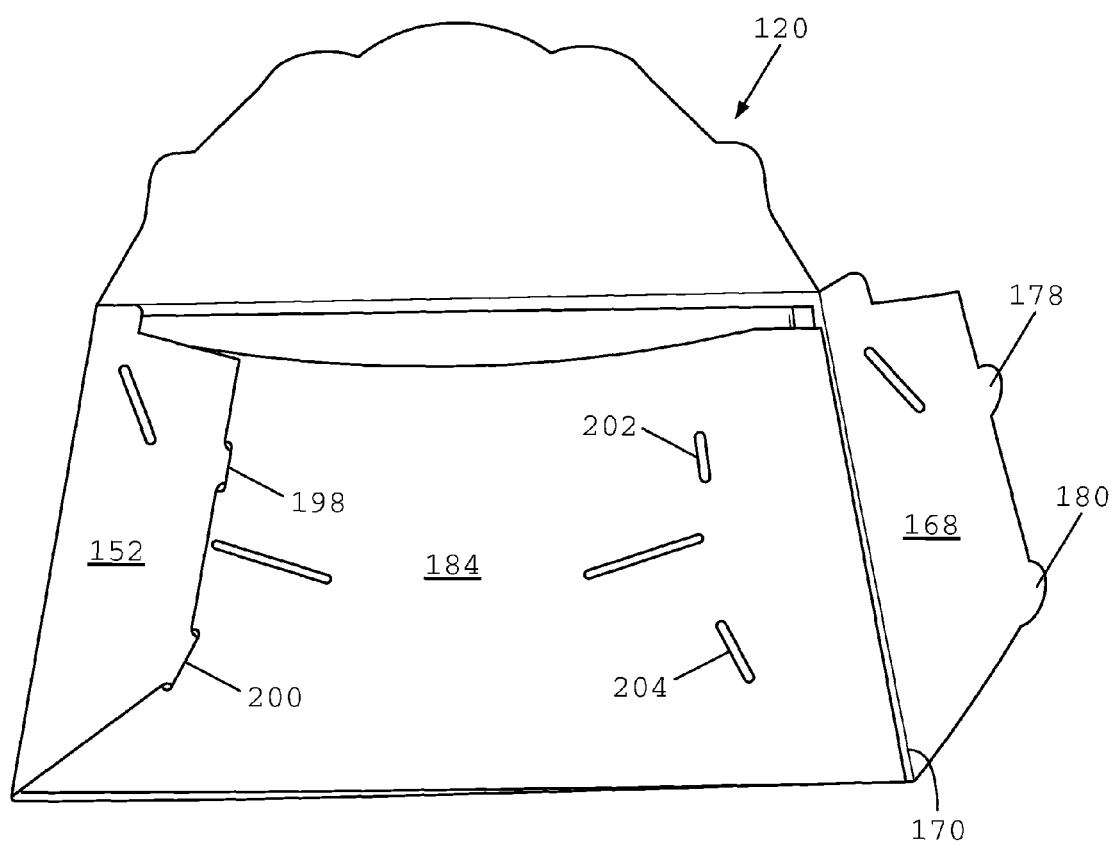

Referring to FIGS. 7C and 7D, in one embodiment, the first side flap 152 is folded over the second panel 184 along a fourth fold line 154 so that an upper locking tab 162 is aligned with a first locking slit 198 and a lower locking tab 164 is aligned with a second locking slit 200. The upper locking tab 162 is preferably inserted into the first locking slit 198 and the lower locking tab 164 is preferably inserted into the second locking slit 200 for mechanically interlocking the first side flap 152 with the second panel 184 in a closed position as shown in FIG. 7D.

Figure 7E:
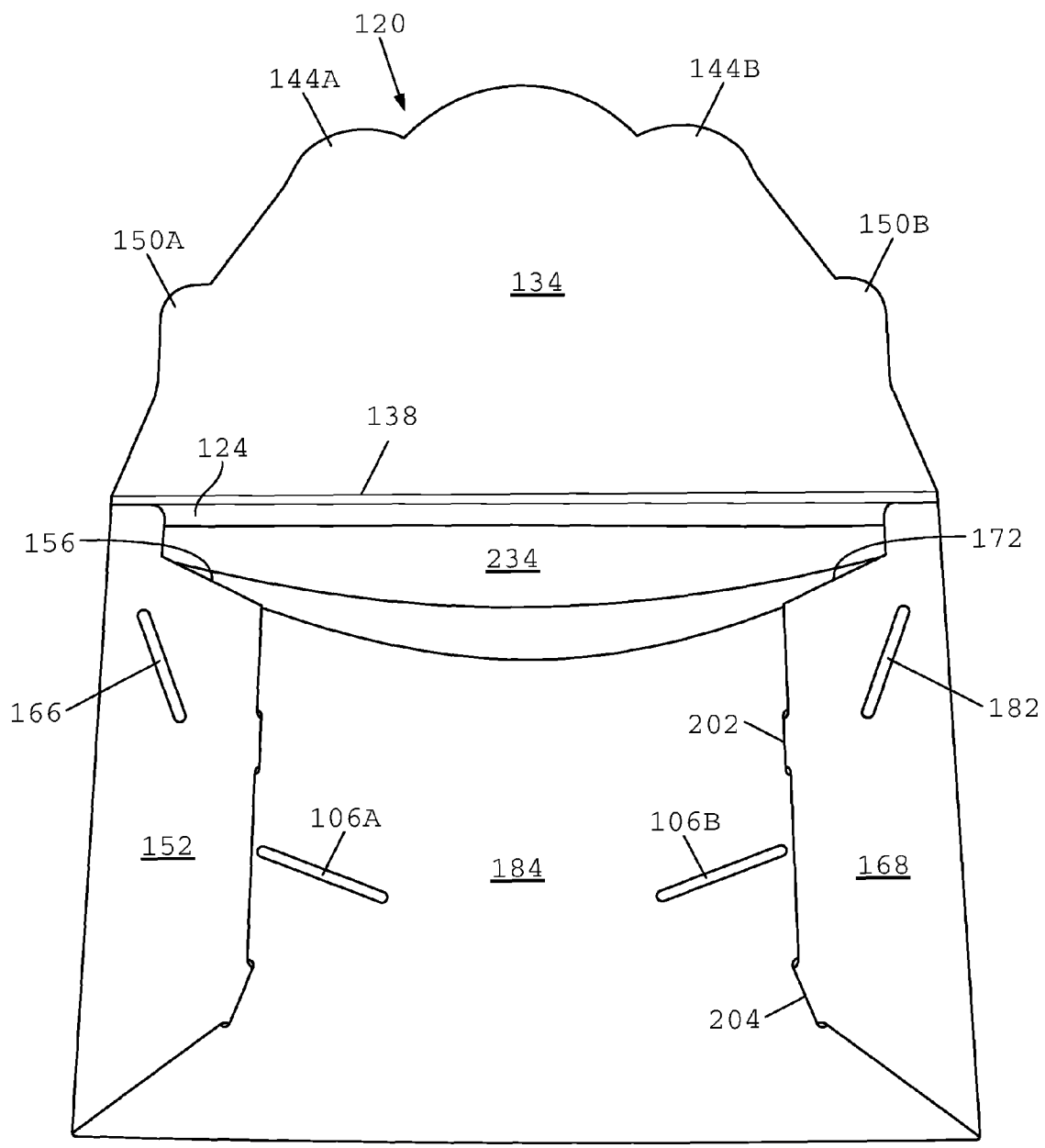

Referring to FIGS. 7D and 7E, in one embodiment, the second side flap 168 is preferably folded over the second panel 184 along the fifth fold line 170 for covering and locking the second side of the box 120. As the second side flap 168 is folded over the second panel 184, an upper locking tab 178 on the second side flap 168 is preferably aligned with a first locking slit 202 on the second panel 184 and a lower locking tab 180 on the second side flap 168 is preferably aligned with a second locking slit 204. The upper locking tab 178 is preferably inserted into the first locking slit 202 and the lower locking tab 180 is preferably inserted into the second locking slit 204 for closing the second side flap 168 over the second side of the box 120 and mechanically interlocking the second side flap 168 with the second panel 184.

After the first and second side flaps 152, 168 have been closed over the respective first and second sides of the box 120, the sealed pouch 234 containing the mesh implant is preferably disposed within the first storage compartment located between the first panel 124 and the third panel 210 (FIG. 7A) of the blank 122. The concave surfaces 156, 172 on the respective first and second side flaps 152, 168 desirably provide better access to the sealed pouch 234 and also provide for more compact folding of the box 120.

Figure 7F:
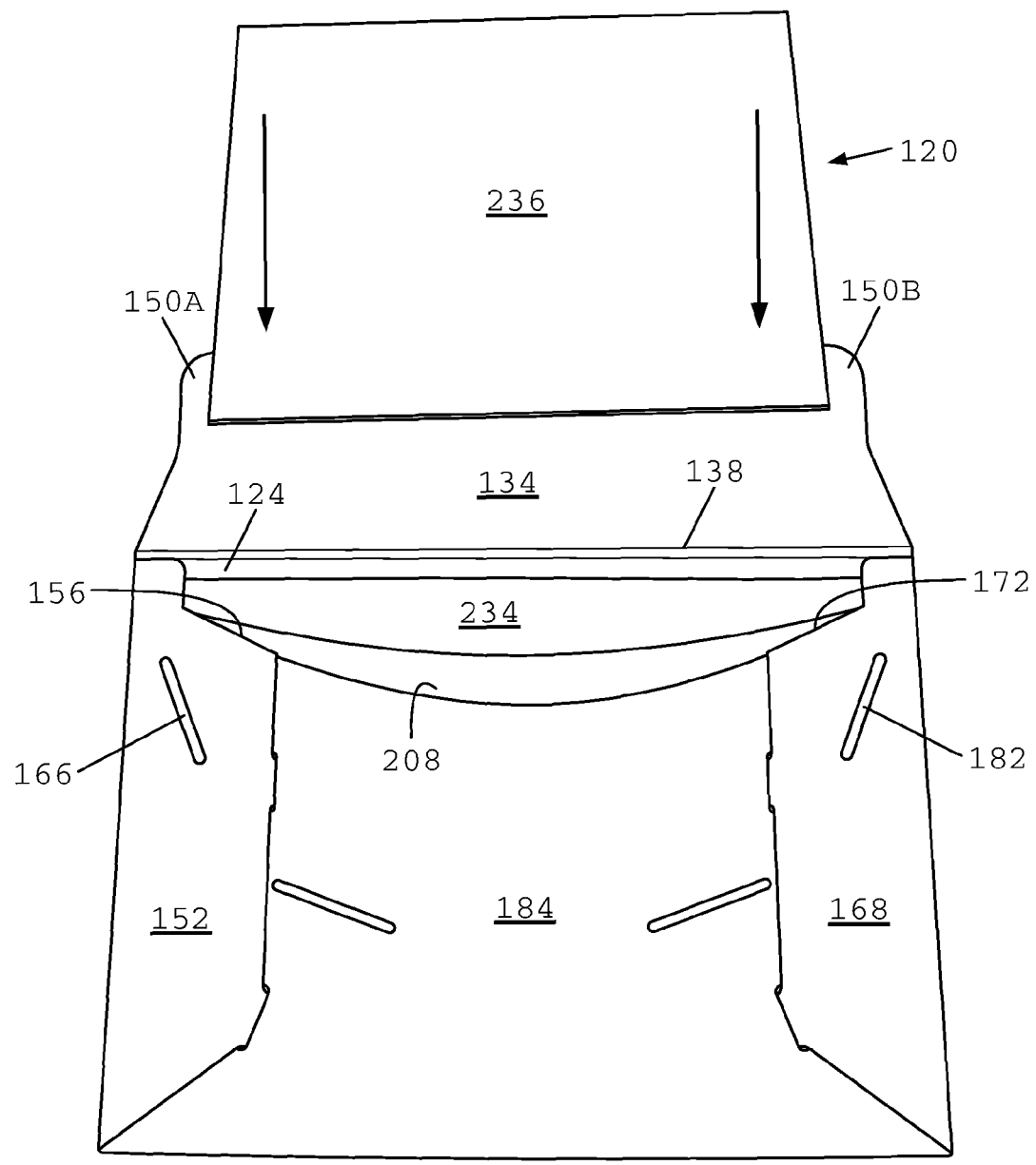

Referring to FIG. 7F, in one embodiment, an instruction manual 236 may be inserted into the second storage compartment by passing the manual 236 though the elongated opening 208 between the second panel 184 and the third panel 210 (FIG. 7A). In one embodiment, the manual 236 is inserted into the second storage compartment in a landscape orientation.

Referring to FIG. 7F, in one embodiment, the concave edges 156, 172 at the upper ends of the side flaps 152, 168 preferably minimize the amount of material between the cover 134 and the second panel 184 so as to reduce the overall thickness of the box 120 when the cover 134 is closed over the second panel 184 for closing the top of the box 120.

Figure 7G:
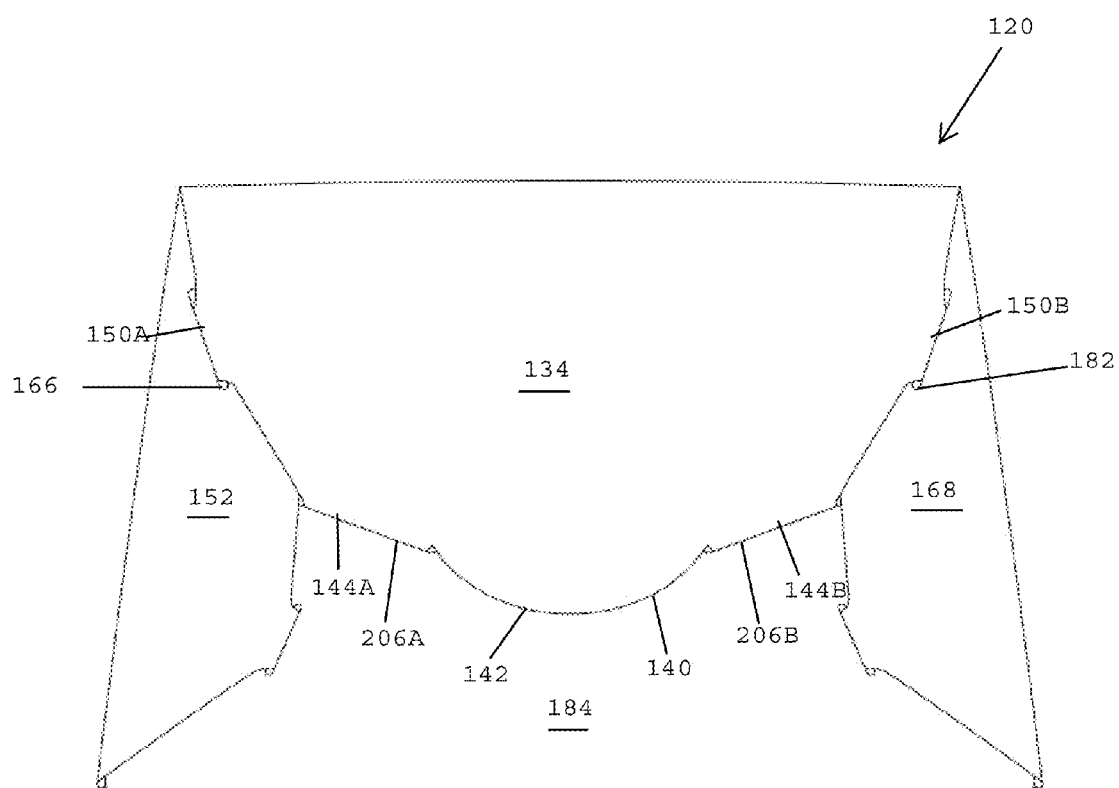

Referring to FIGS. 7F and 7G, in one embodiment, the cover 134 is preferably folded over the second panel 184 and the first and second side flaps 152, 168 covering the sealed pouch 234 and the instruction manual 236 for closing the box 120. In one embodiment, the cover 134 preferably folds along the first fold line 138 extending between the cover 134 and the first panel 124. As the cover 134 is folded for closing the box 120, a first outer locking tab 150A is desirably aligned with a cover locking slit 166 on the first side flap 152 and a second outer locking tab 150B is desirably aligned with a cover locking slit 182 on the second side flap 168. In addition, a first central locking tab 144A is aligned with a first central cover locking slit 206A and a second central locking tab 144B is aligned with a second central cover locking slit 206B. FIG. 7G shows the cover 134 in a closed and locked position with the first outer locking tab 150A inserted into the locking slit 166 on the first side flap 152 and the second outer locking tab 150B inserted into the locking slit 182 on the second side flap 168. In addition, the first central locking tab 144A is inserted into the first central cover locking slit 206A and the second central locking tab 144B is inserted into the second central cover slit 206B. In one embodiment, fold lines may be provided on the respective first and second central locking tabs 144A, 144B to enable the locking tabs to more easily fit within the respective central cover locking slits 206A, 206B, and to prevent tearing or permanent deformation of the cover 134.

Referring to FIG. 7G, in one embodiment, the locking tabs 144A, 144B, 150A, and 150B along the peripheral edge 140 of the cover 134 generally define a first arc extending around the peripheral edge 140 of the cover. The cover locking slits 166, 206A, 206B and 182 on the side flaps and second panel preferably define a second arc that substantially matches the first arc defined by the cover locking tabs. Although the present invention is not limited by any particular theory of operation, it is believed that providing the locking slits in a second arc that substantially conforms to the first arc of the locking tabs results in tighter closing of the cover 134 over the second panel 184 and the side flaps 152, 168, and minimizes the likelihood of damage to the cover 134 or the locking tabs on the cover during closing and opening of the box. In one embodiment, after the cover 134 is closed over the second panel 184 and the side flaps 152, 168, the cover opening tab 142 desirably overlies a surface of the second panel 184.

Figure 8A:
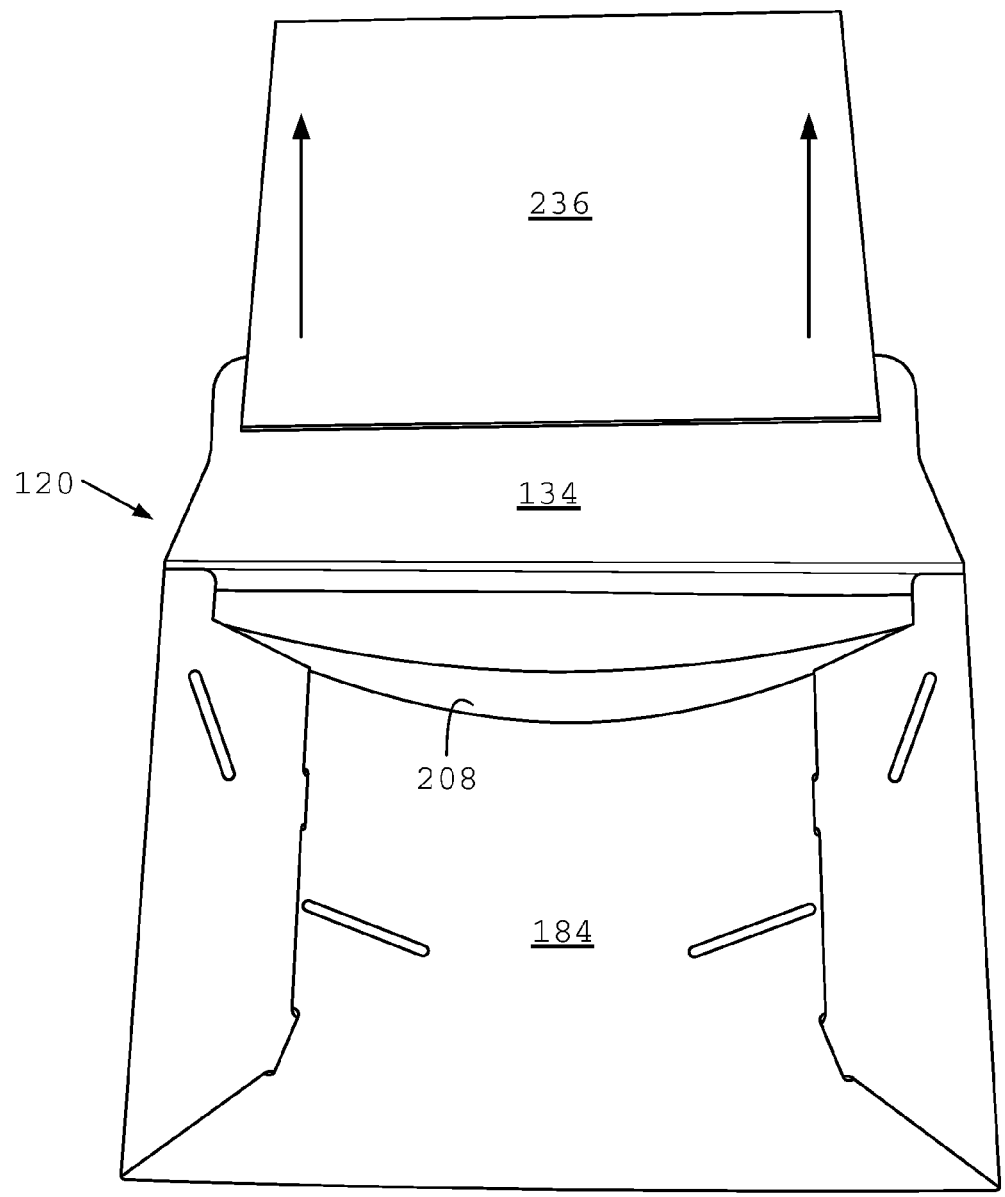
FIGS. 8A-8B show a method of opening a box for accessing a medical device and a booklet, in accordance with one embodiment of the present invention.
Figure 8B:
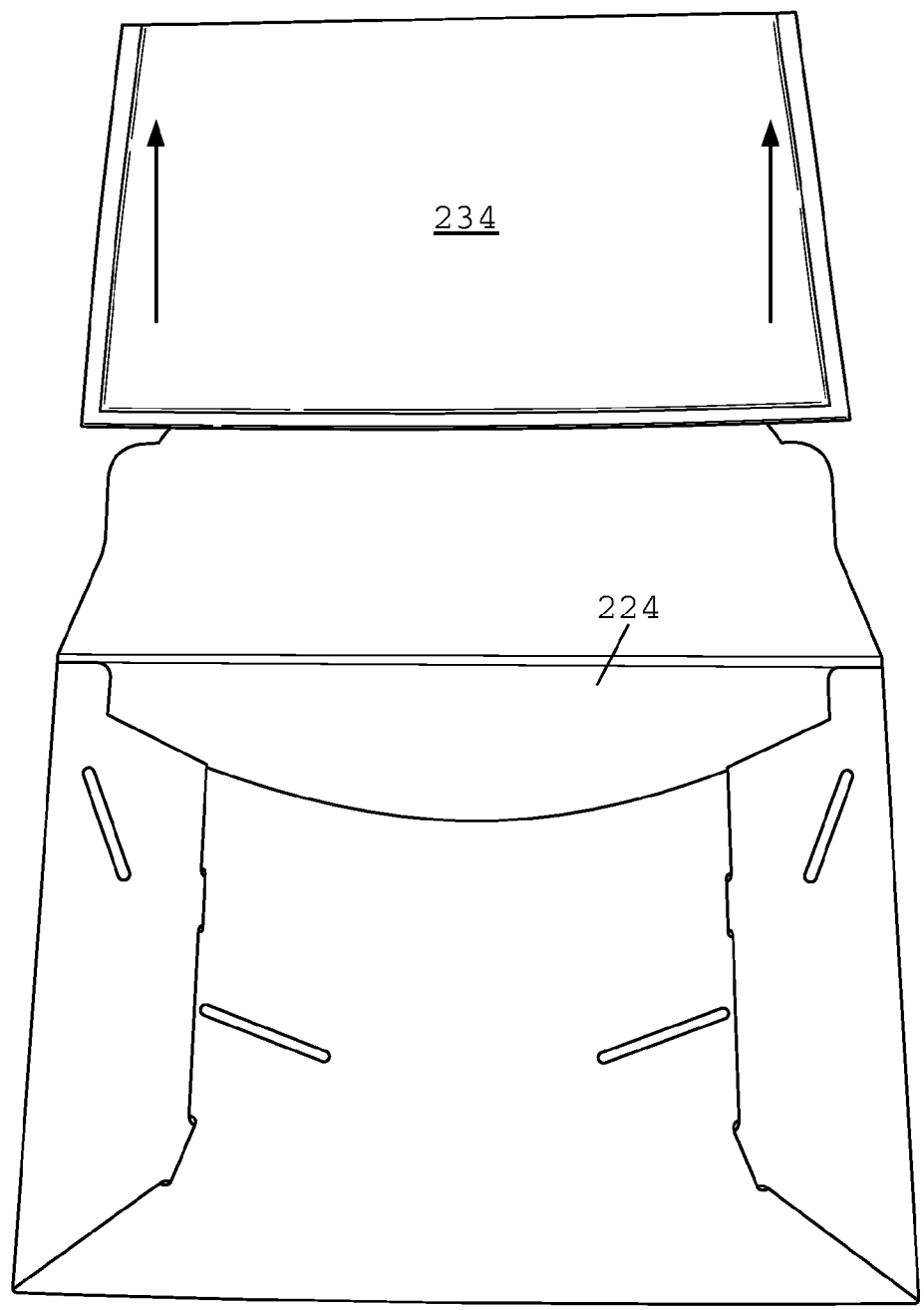

Referring to FIGS. 7G and 8A, in one embodiment, the box 120 is provided to medical personnel during a surgical procedure. The cover 134 may be opened by grasping the cover opening tab 142 so as to unfold the cover relative to the second panel 184. Due to the fold lines provided thereon, the central locking tabs may flex as they are retracted from the opposing locking slits on the second panel.

Referring to FIG. 8A, when the cover 134 has been opened, the instruction manual 236 desirably projects from the pocket opening 208 and the sealed pouch 234 is accessible between the third panel 210 and the first panel 124 of the box. In one embodiment, the instruction manual 236 may be removed from the pocket opening 208 for use by medical personnel. As noted above, the instruction manual preferably includes instructions for using the medical device stored in the pouch 234. Referring to FIG. 8C, after the instruction manual 236 has been removed, the sealed pouch 234 may be removed from the first storage compartment that is disposed between the third panel 210 and the first panel 224 (FIG. 4A).

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:
1. A flat box for storing a medical device comprising:
a first panel having an upper edge, a lower edge, a first side edge, and a second side edge;
a second panel hingedly connected with said lower edge of said first panel, said second panel being foldable over said first panel for defining a storage compartment;
a first side flap hingedly connected with said first side edge of said first panel and being foldable over and interlockable with said second panel for closing a first side of said box;
a second side flap hingedly connected with said second side edge of said first panel and being foldable over and interlockable with said second panel for closing a second side of said box;
a cover hingedly connected with said upper edge of said first panel for moving between an open position for providing access to said storage compartment and a closed position for closing said storage compartment, said cover having a free edge including a plurality of cover locking tabs projecting from said free edge, and each of said first and second side flaps and said second panel including at least one cover locking slit that is adapted to receive at least one of said cover locking tabs, wherein when in the closed position said cover is folded over said first and second side flaps and said second panel, and said cover locking tabs are mechanically interlocked with said cover locking slits on said first and second side flaps and said second panel, wherein said cover locking tabs include first and second central locking tabs and first and second outer locking tabs that are located outside said central locking tabs, and wherein said first and second central locking tabs are hingedly connected with said cover via fold lines disposed at said free edge of said cover and said first and second outer locking tabs are more rigidly connected with said free edge of said cover than said first and second central locking tabs.

2. The flat box as claimed in claim 1, wherein said cover locking tabs at said free edge of said cover define a first arc and said cover locking slits on said first side flap, said second panel, and said second side flap define a second arc that conforms to said first arc.

3. The flat box as claimed in claim 1, wherein said first outer locking tab on said cover is adapted for being mechanically interlocked with a first cover locking slit on said first side flap, said second outer locking tab on said cover is adapted for being mechanically interlocked with a second cover locking slit on said second side flap, and said first and second central locking tabs on said cover are adapted for being mechanically interlocked with a pair of central cover locking slits on said second panel.

4. The flat box as claimed in claim 1, wherein said first side flap includes at least one locking tab and said second panel includes at least one first side flap locking slit adapted to receive said at least one locking tab on said first side flap for mechanically interlocking said first side flap with said second panel.

5. The flat box as claimed in claim 4, wherein said second side flap includes at least one locking tab and said second panel includes at least one second side flap locking slit adapted to receive said at least one locking tab on said second side flap for mechanically interlocking said second side flap with said second panel.

6. The flat box as claimed in claim 5, wherein said at least one first side flap locking slit includes a first locking slit that is parallel to a first side of said second panel and a second locking slit that is angled relative to said first side of said second panel, and wherein said at least one second side locking slit includes a first locking slit that is parallel to a second side of said second panel and a second locking slit that is angled relative to said second side of said second panel.

7. The flat box as claimed in claim 5, wherein said first and second central locking tabs are hingedly connected with said cover so as to be more flexibly connected with said cover than said first and second outer locking tabs.

8. The flat box as claimed in claim 1, further comprising a third panel hingedly connected with a lower edge of said second panel, wherein said third panel is foldable over said second panel for defining a second storage compartment between said second panel and said third panel, and wherein said third panel is adjacent said first panel when said second panel is folded over said first panel.

9. The flat box as claimed in claim 8, wherein when said third panel is folded over said second panel and said second panel is folded over said first panel, said third panel divides said first storage compartment from said second storage compartment.

10. The flat box as claimed in claim 9, wherein said second panel includes an elongated opening extending between major faces of said second panel that provides an access opening for said second storage compartment.

11. The flat box as claimed in claim 10, wherein said elongated opening in said second panel is adapted to hold at least one booklet in said second storage compartment.

12. A flat box for storing a flat medical device comprising:
 a first panel including an upper edge, a lower edge, a first side edge, and a second side edge;
 a second panel hingedly connected with said lower edge of said first panel;
 a third panel hingedly connected with a lower edge of said second panel;
 a first side flap hingedly connected with said first side edge of said first panel;
 a second side flap hingedly connected with said second side edge of said first panel;
 said third panel being foldable over said second panel and said second panel being foldable over said first panel for forming a first storage compartment between said first and third panels and a second storage compartment between said second and third panels;
 said first side flap being foldable over and interlockable with said second panel for closing a first side of said box;
 said second side flap being foldable over and interlockable with said second panel for closing a second side of said box;
 a cover hingedly connected with said upper edge of said first panel, wherein said cover is foldable over and interlockable with said first and second side flaps and said second panel for holding said cover in a closed position, wherein each of said first and second side flaps and said second panel includes at least one cover locking slit adapted to receive a respective locking tab on said cover for mechanically interlocking said cover with said first and second side flaps and said second panel for holding said cover in the closed position, wherein said cover has central locking tabs that engage central cover locking slits on said second panel and outer locking tabs outside said central locking tabs that engage side flap locking slits of said respective first and second side flaps, and wherein said outer locking tabs are more rigidly connected with said cover than said central locking tabs.

13. The flat box as claimed in claim 12, wherein said flat box comprises a foldable paperboard blank including said first, second and third panels, said first and second side flaps, and said cover.

14. The flat box as claimed in claim 12, wherein said upper edge of said first panel and an upper edge of said third panel define an opening for said first storage compartment, and wherein said second panel comprises an elongated opening formed therein defining an opening for said second storage compartment.

15. The flat box as claimed in claim 12, wherein said second panel includes at least one first side flap locking slit adapted to receive at least one locking tab on said first side flap for mechanically interlocking said first side flap with said second panel, and at least one second side flap locking slit adapted to receive at least one locking tab on said second side flap for mechanically interlocking said second side flap with said second panel.

16. The flat box as claimed in claim 12, wherein said cover includes first and second central locking tabs hingedly connected with a free edge of said cover via fold lines, wherein when said cover is closed said first and second central locking tabs are mechanically interlocked with a pair of central cover locking slits on said second panel, a first outer locking tab on said cover is mechanically interlocked with a cover locking slit on said first side flap and a second outer locking tab on said cover is mechanically interlocked with a cover locking slit on said second side flap.

17. The flat box as claimed in claim 16, wherein said cover locking tabs define a first arc and said cover locking slits on said first side flap, said second panel, and said second side flap define a second arc that substantially matches the contour of said first arc.

18. A flat box for storing a surgical mesh comprising:
 a first panel including an upper edge, a lower edge, a first side edge, and a second side edge;
 a second panel hingedly connected with said lower edge of said first panel;
 a third panel hingedly connected with a lower edge of said second panel;
 a first side flap hingedly connected with said first side edge of said first panel;
 a second side flap hingedly connected with said second side edge of said first panel;
 said third panel being foldable over said second panel and said second panel being foldable over said first panel for forming a first storage compartment between said first and third panels and a second storage compartment between said second and third panels;
 a surgical mesh stored in said first storage compartment;
 at least one booklet stored in said second storage compartment;
 said first side flap being foldable over and interlockable with said second panel for closing a first side of said box and holding said second and third panels against said first panel;
 said second side flap being foldable over and interlockable with said second panel for closing a second side of said box and holding said second and third panels against said first panel;
 a cover hingedly connected with said upper edge of said first panel, said cover having a free edge with cover locking tabs, wherein said cover is foldable over said first and second side flaps and said second panel for mechanically interlocking said cover locking tabs with cover locking slits provided on said first and second side flaps and said second panel for holding said cover in a closed position so as to cover said surgical mesh and said at least one booklet, wherein said cover has central locking tabs that engage central cover locking slits on said second panel and outer locking tabs outside said central locking tabs that engage side flap locking slits of said respective first and second side flaps, and wherein said outer locking tabs are more rigidly connected with said cover than said central locking tabs.

19. The flat box as claimed in claim 18, wherein said cover locking tabs define a first arc and said cover locking slits on said first side flap, said second panel, and said second side flap define a second arc that substantially matches the contour of said first arc.

* * * * *